United States Patent [19]
Bjørn et al.

[11] Patent Number: 5,395,922
[45] Date of Patent: Mar. 7, 1995

[54] YEAST PROCESSING SYSTEM

[75] Inventors: Søren Bjørn, Lyngby; Kjeld Norris; Fanny Norris, both of Hellerup, all of Denmark

[73] Assignee: Novo Nordisk A/S, Bagsvaerd, Denmark

[21] Appl. No.: 196,887

[22] Filed: Feb. 15, 1994

Related U.S. Application Data

[63] Continuation of Ser. No. 486,569, Feb. 28, 1990.

[30] Foreign Application Priority Data

Mar. 3, 1989 [DK] Denmark ............... 1054/89
Oct. 6, 1989 [DK] Denmark ............... 4941/89

[51] Int. Cl.⁶ .................. C07K 13/00; C07K 7/40; C12P 21/02
[52] U.S. Cl. .................. 530/350; 530/303; 435/69.1; 435/69.7
[58] Field of Search ............ 435/69.1, 69.7; 935/47, 935/48, 51; 530/350, 303

[56] References Cited

FOREIGN PATENT DOCUMENTS

| | | |
|---|---|---|
| 0123289 | 10/1984 | European Pat. Off. . |
| 0123294 | 10/1984 | European Pat. Off. . |
| 0195680 | 3/1985 | European Pat. Off. . |
| 0206783 | 6/1985 | European Pat. Off. . |
| 0163529 | 12/1985 | European Pat. Off. . |
| 0252854 | 7/1986 | European Pat. Off. . |
| 0281418 | 3/1987 | European Pat. Off. . |
| 0329127 | 2/1988 | European Pat. Off. . |
| 0347845 | 6/1988 | European Pat. Off. . |
| WO 88/10299 | 6/1987 | WIPO . |
| 8901968 | 3/1989 | WIPO . |
| 8902463 | 3/1989 | WIPO . |

OTHER PUBLICATIONS

Zsebo, K. M., et al. (1986) J. Biol. Chem. 261 (13), 5858–5865.
Kurjan, J., et al. (1982) Cell 30, 933–943.
Biological Abstract, 12824.
Thim et al., Proc. Natl. Acad. Sci. USA, vol. 83, pp. 6766–6770 (1986).

*Primary Examiner*—Charles L. Patterson, Jr.
*Attorney, Agent, or Firm*—Steve T. Zelson; Cheryl H. Agris

[57] ABSTRACT

A polypeptide for production in yeast comprises a fusion of a signal peptide, a leader peptide and a heterologous protein or polypeptide. The polypeptide is modified in its amino acid sequence adjacent to a yeast processing site positioned between the C-terminal end of the leader peptide and the N-terminal end of the heterologous protein so as to provide a presentation of the processing site which makes it accessible to proteolytic cleavage. Such a presentation is provided by adding one or more amino acids (at least one of which is negatively charged) to either the C-terminal end of the leader or the N-terminal end of the protein, or both. The heterologous protein may, for instance, be aprotinin or insulin precursor or an analogue thereof.

46 Claims, 18 Drawing Sheets

```
                    1               5                       10
     MetAlaLysArgArgProAspPheCysLeuGluProProTyrThrGly
    NcoI         StuI
    CATGGCCAAAAGAAGGCCTGATTTCTGTTTGGAACCTCCATACACTGGT
        CGGTTTTCTTCCGGACTAAAGACAAACCTTGGAGGTATGTGACCA 15              20              25
     ProCysLysAlaArgIleIleArgTyrPheTyrAsnAlaLysAlaGly

CCATGTAAAGCTAGAATCATCAGATACTTCTACAACGCCAAGGCTGGT
    GGTACATTTCGATCTTAGTAGTCTATGAAGATGTTGCGGTTCGACCA 30              35              40
     LeuCysGlnThrPheValTyrGlyGlyCysArgAlaLysArgAsnAsn

TTGTGTCAAACTTTCGTTTACGGTGGCTGCAGAGCTAAGAGAAACAAC
    AACACAGTTTGAAAGCAAATGCCACCGACGTCTCGATTCTCTTTGTTG 45              50              55    58
     PheLysSerAlaGluAspCysMetArgThrCysGlyGlyAlaStop
                                               XbaI
    TTCAAGTCTGCTGAAGACTGCATGAGAACTTGTGGTGGTGCCTAAT
    AAGTTCAGACGACTTCTGACGTACTCTTGAACACCACCACGGATTAGATC
```

Fig. 1

```
         10        20        30        40        50        60
          |         |         |         |         |         |
     GAATTCCATTCAAGAATAGTTCAAACAAGAAGATTACAAACTATCAATTTCATACACAAT 70        80        90       100       110       120
          |         |         |         |         |         |
     ATAAACGACCAAAAGAATGAAGGCTGTTTTCTTGGTTTTGTCCTTGATCGGATTCTGCTG
                     METLysAlaValPheLeuValLeuSerLeuIleGlyPheCysTrp 130       140       150       160       170       180
          |         |         |         |         |         |
     GGCCCAACCAGTCACTGGCGATGAATCATCTGTTGAGATTCCGGAAGAGTCTCTGATCAT
     AlaGlnProValThrGlyAspGluSerSerValGluIleProGluGluSerLeuIleIle 190       200       210       220       230       240
          |         |         |         |         |         |
     CGCTGAAAACACCACTTTGGCTAACGTCGCCATGGCTAAGAGAGAATTGAGACCTGATTT
     AlaGluAsnThrThrLeuAlaAsnValAlaMETAlaLysArgGluLeuArgProAspPhe
                                                ↑

250       260       270       280       290       300
          |         |         |         |         |         |
     CTGTTTGGAACCTCCATACACTGGTCCATGTAAAGCTAGAATCATCAGATACTTCTACAA
     CysLeuGluProProTyrThrGlyProCysLysAlaArgIleIleArgTyrPheTyrAsn 310       320       330       340       350       360
          |         |         |         |         |         |
     CGCCAAGGCTGGTTTGTGTCAAACTTTCGTTTACGGTGGCTGCAGAGCTAAGAGAAACAA
     AlaLysAlaGlyLeuCysGlnThrPheValTyrGlyGlyCysArgAlaLysArgAsnAsn 370       380       390       400       410
          |         |         |         |         |
     CTTCAAGTCTGCTGAAGACTGCATGAGAACTTGTGGTGGTGCCTAATCTAGA
     PheLysSerAlaGluAspCysMETArgThrCysGlyGlyAla
```

Fig. 4

```
            10        20        30        40        50        60
             |         |         |         |         |         |
          GAATTCCATTCAAGAATAGTTCAAACAAGAAGATTACAAACTATCAATTTCATACACAAT 70        80        90       100       110       120
             |         |         |         |         |         |
          ATAAACGACCAAAAGAATGAAGGCTGTTTTCTTGGTTTTGTCCTTGATCGGATTCTGCTG

METLysAlaValPheLeuValLeuSerLeuIleGlyPheCysTrp 130       140       150       160       170       180
             |         |         |         |         |         |
          GGCCCAACCAGTCACTGGCGATGAATCATCTGTTGAGATTCCGGAAGAGTCTCTGATCAT

AlaGlnProValThrGlyAspGluSerSerValGluIleProGluGluSerLeuIleIle 190       200       210       220       230       240
             |         |         |         |         |         |
          CGCTGAAAACACCACTTTGGCTAACGTCGCCATGGCTAAGAGAGAATTGGACTTGAGACC

AlaGluAsnThrThrLeuAlaAsnValAlaMETAlaLysArgGluLeuAspLeuArgPro
                                                    ↑

250       260       270       280       290       300
             |         |         |         |         |         |
          TGATTTCTGTTTGGAACCTCCATACACTGGTCCATGTAAAGCTAGAATCATCAGATACTT

AspPheCysLeuGluProProTyrThrGlyProCysLysAlaArgIleIleArgTyrPhe 310       320       330       340       350       360
             |         |         |         |         |         |
          CTACAACGCCAAGGCTGGTTTGTGTCAAACTTTCGTTTACGGTGGCTGCAGAGCTAAGAG

TyrAsnAlaLysAlaGlyLeuCysGlnThrPheValTyrGlyGlyCysArgAlaLysArg 370       380       390       400       410
             |         |         |         |         |
          AAACAACTTCAAGTCTGCTGAAGACTGCATGAGAACTTGTGGTGGTGCCTAATCTAGA

AsnAsnPheLysSerAlaGluAspCysMETArgThrCysGlyGlyAla
```

Fig. 7

```
         10        20        30        40        50        60
          |         |         |         |         |         |
GAATTCCATTCAAGAATAGTTCAAACAAGAAGATTACAAACTATCAATTTCATACACAAT 70        80        90       100       110       120
          |         |         |         |         |         |
ATAAACGACCAAAAGAATGAAGGCTGTTTTCTTGGTTTTGTCCTTGATCGGATTCTGCTG
                  METLysAlaValPheLeuValLeuSerLeuIleGlyPheCysTrp 130       140       150       160       170       180
          |         |         |         |         |         |
GGCCCAACCAGTCACTGGCGATGAATCATCTGTTGAGATTCCGGAAGAGTCTCTGATCAT
AlaGlnProValThrGlyAspGluSerSerValGluIleProGluGluSerLeuIleIle 190       200       210       220       230       240
          |         |         |         |         |         |
CGCTGAAAACACCACTTTGGCTAACGTCGCCATGGCTAAGGAATTGGAGAAGAGAAGGCC
AlaGluAsnThrThrLeuAlaAsnValAlaMETAlaLysGluLeuGluLysArgArgPro
                                                         ↑

250       260       270       280       290       300
          |         |         |         |         |         |
TGATTTCTGTTTGGAACCTCCATACACTGGTCCATGTAAAGCTAGAATCATCAGATACTT
AspPheCysLeuGluProProTyrThrGlyProCysLysAlaArgIleIleArgTyrPhe 310       320       330       340       350       360
          |         |         |         |         |         |
CTACAACGCCAAGGCTGGTTTGTGTCAAACTTTCGTTTACGGTGGCTGCAGAGCTAAGAG
TyrAsnAlaLysAlaGlyLeuCysGlnThrPheValTyrGlyGlyCysArgAlaLysArg 370       380       390       400       410
          |         |         |         |         |
AAACAACTTCAAGTCTGCTGAAGACTGCATGAGAACTTGTGGTGGTGCCTAATCTAGA
AsnAsnPheLysSerAlaGluAspCysMETArgThrCysGlyGlyAla
```

Fig. 9

```
       10        20        30        40        50        60
        |         |         |         |         |         |
GAATTCCATTCAAGAATAGTTCAAACAAGAAGATTACAAACTATCAATTTCATACACAAT 70        80        90       100       110       120
        |         |         |         |         |         |
ATAAACGACCAAAAGAATGAAGGCTGTTTTCTTGGTTTTGTCCTTGATCGGATTCTGCTG
                  METLysAlaValPheLeuValLeuSerLeuIleGlyPheCysTrp 130       140       150       160       170       180
        |         |         |         |         |         |
GGCCCAACCAGTCACTGGCGATGAATCATCTGTTGAGATTCCGGAAGAGTCTCTGATCAT
AlaGlnProValThrGlyAspGluSerSerValGluIleProGluGluSerLeuIleIle 190       200       210       220       230       240
        |         |         |         |         |         |
CGCTGAAAACACCACTTTGGCTAACGTCGCCATGGCTGAGAGATTGGAGAAGAGAAGGCC
AlaGluAsnThrThrLeuAlaAsnValAlaMETAlaGluArgLeuGluLysArgArgPro
  *                                                    ↑

250       260       270       280       290       300
        |         |         |         |         |         |
TGATTTCTGTTTGGAACCTCCATACACTGGTCCATGTAAAGCTAGAATCATCAGATACTT
AspPheCysLeuGluProProTyrThrGlyProCysLysAlaArgIleIleArgTyrPhe 310       320       330       340       350       360
        |         |         |         |         |         |
CTACAACGCCAAGGCTGGTTTGTGTCAAACTTTCGTTTACGGTGGCTGCAGAGCTAAGAG
TyrAsnAlaLysAlaGlyLeuCysGlnThrPheValTyrGlyGlyCysArgAlaLysArg 370       380       390       400       410
        |         |         |         |         |
AAACAACTTCAAGTCTGCTGAAGACTGCATGAGAACTTGTGGTGGTGCCTAATCTAGA
AsnAsnPheLysSerAlaGluAspCysMETArgThrCysGlyGlyAla
```

Fig. 11

```
              3         5                  10                 15
          AspPheCysLeuGluProProTyrThrGlyProCysLysAlaArgIle
    AAAGAGATTTCTGTTTGGAACCTCCATACACTGGTCCATGTAAAGCTAGAATC
        CTAAAGACAAACCTTGGAGGTATGTGACCAGGTACATTTCGATCTTAG 20                25                 30                35
          IleArgTyrPheTyrAsnAlaLysAlaGlyLeuCysGlnThrPheValTyrGly
    ATCAGATACTTCTACAACGCCAAGGCTGGTTTGTGTCAAACTTTCGTTTACGGT
    TAGTCTATGAAGATGTTGCGGTTCGACCAAACACAGTTTGAAAGCAAATGCCA 40                45                50
          GlyCysArgAlaLysArgAsnAsnPheLysSerAlaGluAspCysMetArgThr
    GGCTGCAGAGCTAAGAGAAACAACTTCAAGTCTGCTGAAGACTGCATGAGAACT
    CCGACGTCTCGATTCTCTTTGTTGAAGTTCAGACGACTTCTGACGTACTCTTGA 55       58
    CysGlyGlyAlaStopXbaI
    TGTGGTGGTGCCTAAT
    ACACCACCACGGATTAGATC
```

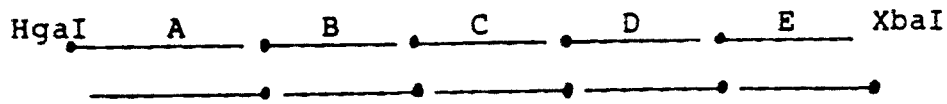

Fig. 12

```
         10        20        30        40        50        60
          |         |         |         |         |         |
GAATTCCATTCAAGAATAGTTCAAACAAGAAGATTACAAACTATCAATTTCATACACAAT 70        80        90       100       110       120
          |         |         |         |         |         |
ATAAACGACCAAAAGAATGAAGGCTGTTTTCTTGGTTTTGTCCTTGATCGGATTCTGCTG

METLysAlaValPheLeuValLeuSerLeuIleGlyPheCysTrp 130       140       150       160       170       180
          |         |         |         |         |         |
GGCCCAACCAGTCACTGGCGATGAATCATCTGTTGAGATTCCGGAAGAGTCTCTGATCAT

AlaGlnProValThrGlyAspGluSerSerValGluIleProGluGluSerLeuIleIle 190       200       210       220       230       240
          |         |         |         |         |         |
CGCTGAAAACACCACTTTGGCTAACGTCGCCATGGCTAAGGAATTGGAAAAGAGATTCGT

AlaGluAsnThrThrLeuAlaAsnValAlaMETAlaLysGluLeuGluLysArgPheVal
                                                          ↑

250       260       270       280       290       300
          |         |         |         |         |         |
TAACCAACACTTGTGCGGTTCCCACTTGGTTGAAGCTTTGTACTTGGTTTGCGGTGAAAG

AsnGlnHisLeuCysGlySerHisLeuValGluAlaLeuTyrLeuValCysGlyGluArg 310       320       330       340       350       360
          |         |         |         |         |         |
AGGTTTCTTCTACACTCCTAAGGCTGCTAAGGGTATTGTCGAACAATGCTGTACCTCCAT

GlyPhePheTyrThrProLysAlaAlaLysGlyIleValGluGlnCysCysThrSerIle 370       380       390       400       410
          |         |         |         |         |
CTGCTCCTTGTACCAATTGGAAAACTACTGCAACTAGACGCAGCCCGCAGGCTCTAGA

CysSerLeuTyrGlnLeuGluAsnTyrCysAsn
```

Fig. 16

```
         10        20        30        40        50        60
          |         |         |         |         |         |
       GAATTCCATTCAAGAATAGTTCAAACAAGAAGATTACAAACTATCAATTTCATACACAAT 70        80        90       100       110       120
          |         |         |         |         |         |
       ATAAACGATTAAAAGAATGAGATTTCCTTCAATTTTTACTGCAGTTTTATTCGCAGCATC
                        METArgPheProSerIlePheThrAlaValLeuPheAlaAlaSer 130       140       150       160       170       180
          |         |         |         |         |         |
       CTCCGCATTAGCTGCTCCAGTCAACACTACAACAGAAGATGAAACGGCACAAATTCCGGC
       SerAlaLeuAlaAlaProValAsnThrThrThrGluAspGluThrAlaGlnIleProAla 190       200       210       220       230       240
          |         |         |         |         |         |
       TGAAGCTGTCATCGGTTACTTAGATTTAGAAGGGGATTTCGATGTTGCTGTTTTGCCATT
       GluAlaValIleGlyTyrLeuAspLeuGluGlyAspPheAspValAlaValLeuProPhe 250       260       270       280       290       300
          |         |         |         |         |         |
       TTCCAACAGCACAAATAACGGGTTATTGTTTATAAATACTACTATTGCCAGCATTGCTGC
       SerAsnSerThrAsnAsnGlyLeuLeuPheIleAsnThrThrIleAlaSerIleAlaAla 310       320       330       340       350       360
          |         |         |         |         |         |
       TAAAGAAGAAGGGGTATCTTTGGATAAAAGAGAAGTTAACCAACACTTGTGCGGTTCCCA
       LysGluGluGlyValSerLeuAspLysArgGluValAsnGlnHisLeuCysGlySerHis
                                    ↑

370       380       390       400       410       420
          |         |         |         |         |         |
       CTTGGTTGAAGCTTTGTACTTGGTTTGCGGTGAAAGAGGTTTCTTCTACGAACCTAAGGC
       LeuValGluAlaLeuTyrLeuValCysGlyGluArgGlyPhePheTyrGluProLysAla 430       440       450       460       470       480
          |         |         |         |         |         |
       TGCTAAGGGTATTGTCGAACAATGCTGTACCTCCATCTGCTCCTTGTACCAATTGGAAAA
       AlaLysGlyIleValGluGlnCysCysThrSerIleCysSerLeuTyrGlnLeuGluAsn 490       500       510
          |         |         |
       CTACTGCAACTAGACGCAGCCCGCAGGCTCTAGA
       TyrCysAsn
```

YEAST PROCESSING SYSTEM

This application is a continuation application of co-pending application Ser. No. 07/486,569, filed Feb. 28, 1990.

FIELD OF INVENTION to polypeptides expressed and processed in yeast, a DNA construct comprising a DNA sequence encoding such polypeptides, vectors carrying such DNA fragments and yeast cells transformed with the vectors, as well as a process of producing heterologous proteins in yeast.

BACKGROUND OF THE INVENTION

Yeast organisms produce a number of proteins synthesized intracellularly, but having a function outside the cell. Such extracellular proteins are referred to as secreted proteins. These secreted proteins are expressed initially inside the cell in a precursor or a pre-protein form containing a presequence ensuring effective direction of the expressed product across the membrane of the endoplasmic reticulum (ER). The presequence, normally named a signal peptide, is generally cleaved off from the desired product during translocation. Once entered in the secretory pathway, the protein is transported to the Golgi apparatus. From the Golgi the protein can follow different routes that lead to compartments such as the cell vacuole or the cell membrane, or it can be routed out of the cell to be secreted to the external medium (Pfeffer, S. R. and Rothman, J. E. *Ann. Rev. Biochem.* 56 (1987), 829–852).

Several approaches have been suggested for the expression and secretion in yeast of proteins heterologous to yeast. European published patent application No. 0088632A describes a process by which proteins heterologous to yeast are expressed, processed and secreted by transforming a yeast organism with an expression vehicle harbouring DNA encoding the desired protein and a signal peptide, preparing a culture of the transformed organism, growing the culture and recovering the protein from the culture medium. The signal peptide may be the desired proteins own signal peptide, a heterologous signal peptide or a hybrid of native and heterologous signal peptide.

A problem encountered with the use of signal peptides heterologous to yeast might be that the heterologous signal peptide does not ensure efficient translocation and/or cleavage after the signal peptide.

The *S. cerevisiae* MFα1 (α-factor) is synthesized as a prepro form of 165 amino acids comprising a 19 amino acids long signal- or prepeptide followed by a 64 amino acids long "leader" or propeptide, encompassing three N-linked glycosylation sites followed by (LysArg-(Asp/Glu, Ala)$_{2-3}$α-factor)$_4$ (Kurjan, J. and Herskowitz, I. *Cell* 30 (1982), 933–943). The signal-leader part of the preproMFα1 has been widely employed to obtain synthesis and secretion of heterologous proteins in *S. cerivisiae*.

Use of signal/leader peptides homologous to yeast is known from among others U.S. Pat. No. 4,546,082, European published patent applications Nos. 0116201A, 0123294A, 0123544A, 0163529A, and 0123289A and DK patent specifications Nos. 2484/84 and 3614/83.

In EP 0123289A utilization of the *S. cerevisiae* a-factor precursor is described whereas DK 2484/84 describes utilization of the *Saccharomyces cerevisiae* invertase signal peptide and DK 3614/83 utilization of the *Saccharomyces cerevisiae* PH05 signal peptide for secretion of foreign proteins.

U.S. Pat. No. 4,546,082, EP 0016201A, 0123294A, 0123544A, and 0163529A describe processes by which the α-factor signal-leader from Saccharomyces cerevisiae *(MFα1* or MFα2) is utilized in the secretion process of expressed heterologous proteins in yeast. By fusing a DNA sequence encoding coding the *S. cerevisiea* MFα1 signal/leader sequence at the 5' end of the gene for the desired protein secretion and processing of the desired protein was demonstrated.

EP 206,783 discloses a system for the secretion of polypeptides from *S. serevisiae* whereby the α-factor leader sequence has been truncated to eliminate the four α-factor peptides present on the native leader sequence so as to leave the leader peptide itself fused to a heterologous polypeptide via the α-factor processing site LysArgGluAlaGluAla. This construction is indicated to lead to an efficient process of smaller peptides (less than 50 amino acids). For the secretion and processing of larger polypeptides, the native α-factor leader sequence has been truncated to leave one or two α-factor peptides between the leader peptide and the polypeptide.

A number of secreted proteins are routed so as to be exposed to a proteolytic processing system which can cleave the peptide bond at the carboxy end of two consecutive basic amino acids. This enzymatic activity is in *S. cerevisiae* encoded by the KEX 2 gene (Julius, D. A. et al., *Cell* 37 (1984b), 1075). Processing of the product by the KEX 2 gene product is needed for the secretion of active *S, cerevisiae* mating factor α1 (MFα1 or α-factor) but is not involved in the secretion of active *S. cerevisiae* mating factor a.

Secretion and correct processing of a polypeptide intended to be secreted is obtained in some cases when culturing a yeast organism which is transformed with a vector constructed as indicated in the references given above. In many cases, however, the level of secretion is very low or there is no secretion, or the proteolytic processing may be incorrect or incomplete. The present inventors currently believe this to be ascribable, to some extent, to an insufficient exposure of the processing site present between the C-terminal end of the leader peptide and the N-terminal end of the heterologous protein so as to render it inaccessible or, at least, less accessible to proteolytic cleavage.

SUMMARY OF THE INVENTION

It has surprisingly been found that by providing certain modifications near the processing site at the C-terminal end of the leader peptide and/or the N-terminal end of a heterologous polypeptide fused to the leader peptide, it is possible to obtain a higher yield of the correctly processed protein than is obtainable with unmodified leader peptide-heterologous polypeptide constructions.

Accordingly, the present invention relates to a polypeptide comprising a fusion of a signal peptide, a leader peptide and a heterologous protein or polypeptide, which polypeptide is modified in its amino acid sequence adjacent to a yeast processing site positioned between the C-terminal end of the leader peptide and the N-terminal end of the heterologous protein so as to provide a presentation of the processing site which makes it accessible to proteolytic cleavage, the polypeptide having the following structure signal peptide-leader peptide-$X^1$-$X^2$-$X^3$-$X^4$-heterologous protein wherein $X^1$ is a peptide bond or represents one or more amino acids which may be the same or different, $X^2$ and $X^3$ are the same or different and represent a basic amino acid selected from the group consisting of Lys and Arg, $X^2$ and $X^3$ together defining a yeast processing site, and $X^4$ is a peptide bond or represents one or more amino acids which may be the same or different, with the proviso that $X^1$ and/or $X^4$ represent one or more amino acids and that at least one of the amino acids represented by $X^1$ and/or $X^4$ is a negatively charged amino acid selected from the group consisting of Glu and Asp.

In the present context, the term "signal peptide" is understood to mean a presequence which is predominantly hydrophobic in nature and present as an N-terminal sequence on the precursor form of an extracellular protein expressed in yeast. The function of the signal peptide is to allow the heterologous protein to be secreted to enter the endoplasmic reticulum. The signal peptide is normally cleaved off in the course of this process. The signal peptide may be heterologous or homologous to the yeast organism producing the protein but, as explained above, a more efficient cleavage of the signal peptide may be obtained when it is homologous to the yeast organism in question.

The expression "leader peptide" is understood to indicate a predominantly hydrophilic peptide whose function is to allow the heterologous protein to be secreted to be directed from the endoplasmic reticulum to the Golgi apparatus and further to a secretory vesicle for secretion into the medium, (i.e. exportation of the expressed protein or polypeptide across the cell wall or at least through the cellular membrane into the periplasmic space of the cell).

The expression "heterologous protein or polypeptide" is intended to indicate a protein or polypeptide which is not produced by the host yeast organism in nature. The terms "protein" and "polypeptide" are used substantially interchangeably in the following description.

The modification of the polypeptide at the processing site (the site at which the leader peptide is removed from the heterologous protein by proteolytic cleavage provided by yeast proteolytic enzymes), which modification is represented by $X^1$ and/or $X^4$ may be in the form of an extension, substitution or deletion of one or more amino acids at the C-terminal end of the leader peptide and/or at the N-terminal end of the heterologous protein.

In accordance with the invention, it has surprisingly been found that a more efficient and correct processing of the heterologous protein may be obtained when at least one of the amino acids with which the sequence of the polypeptide has been extended or by which one or more of the native amino acids in the sequence have been substituted is a negatively charged amino acid such as the ones indicated above. A similar effect is observed when a negatively charged amino acid is provided in the proximity to the processing site by deletion, i.e. by deleting one or more amino acids from the C-terminal end of the leader or from the N-terminal end of the protein sequence until a negatively charged amino acid is present adjacent to the processing site.

Without wishing to be limited to any particular theory, it is assumed that this effect may be ascribed to the increased hydrophilicity imposed by the negatively charged amino acids adjacent to the processing site, which results in enhanced exposure of the tertiary structure of the polypeptide at the processing site in the aqueous intracellular environment and therefore more accessible to proteolytic cleavage by the processing enzyme. The advantageous effect of negatively charged amino acids, in contrast to positively charged or neutral amino acids, may be ascribed to the negatively charged side chains of these amino acids which contribute to the hydrophilicity of the tertiary structure at the processing site without giving rise to any potential inhibition of the processing enzyme.

It is also possible that negatively charged amino acids contribute to creating and maintaining a tertiary structure at the processing site (e.g. turns, hairpins or loop structures) by other means such as by interaction with other amino acid residues in the polypeptide. Furthermore, direct interaction between negatively charged amino acids and the processing enzyme could also take place. Thus, it is believed that negatively charged amino acids positioned adjacent to the two basic amino acids of the processing site may direct the processing enzyme to carry out a correct and efficient cleavage by charge interactions between proteins and/or between protein and solvent.

In another aspect, the present invention relates to a DNA construct which comprises a DNA sequence encoding the polypeptide defined above.

In a further aspect, the invention relates to a recombinant expression vector which is capable of replicating in yeast and which carries a DNA construct encoding the above-defined polypeptide, as well as a yeast strain which is capable of expressing the heterologous protein or polypeptide and which is transformed with this vector.

In a still further aspect, the invention relates to a process for producing a heterologous protein or polypeptide in yeast, comprising cultivating the transformed yeast strain in a suitable medium to obtain expression and secretion of the heterologous protein or polypeptide, after which the protein or polypeptide is isolated from the medium.

DETAILED DISCLOSURE OF THE INVENTION

Consistent with the explanation given above, when $X^1$ represents a single amino acid, this is Glu or Asp.

$X^1$ and/or $X^4$ suitably represent 1-6 amino acids. When $X^1$ represents a sequence of two amino acids, it may have the structure BA, wherein A is Glu or Asp, and B is Glu, Asp, Val, Gly or Leu, for instance LeuGlu.

When $X^1$ represents a sequence of three amino acids, it may have the structure CBA, wherein A and B are as defined above, and C is Glu, Asp, Pro, Gly, Val, Leu, Arg or Lys, for instance AspLeuGlu.

When $X^1$ represents a sequence of more than two amino acids, one of the additional amino acids may suitably be Pro or Gly as these amino acids are known to introduce and/or form part of turns, hairpins and loop structures likely to facilitate the accessibility of the processing site to the proteolytic enzyme.

When $X^1$ represents a sequence of four amino acids, it may have the structure DCBA, wherein A, B and C are as defined above, and D has the same meanings as C, for instance GluArgLeuGlu, LysGluLeuGlu or LeuAspLeuGlu.

When $X^1$ represents a sequence of five amino acids, it may have the structure EDCBA, wherein A, B, C and D are as defined above, and E has the same meanings as C, for instance LeuGluArgLeuGlu.

When $X^1$ represents a sequence of six amino acids, it may have the structure FEDCBA, wherein A, B, C, D and E are as defined above, and F has the same meanings as C, for instance ValLeuGluArgLeuGlu.

It will be understood that other combinations of amino acids are possible as a meaning of $X^1$ without departing from the scope of the invention, provided that at least one of the amino acids in the sequence is a negatively charged amino acid, as explained above.

Suitable meanings of $X^4$ may be the ones shown above for $X^1$, though the order of the amino acids will typically be reversed (i.e. ABC rather than CBA, etc.).

In embodiments of the polypeptide of the invention where the heterologous protein is initiated by one or more positively charged or hydrophobic amino acids, $X^4$ advantageously represents one or more amino acids rather than a peptide bond as this is thought to ensure a greater accessibility of the processing site to proteolytic enzymes.

In cases where $X^4$ represents an N-terminal extension of 1-6 amino acids, it may be suitable to provide an additional processing site between the amino acid or acids represented by $X^4$ and the N-terminal end of the heterologous protein. This is particularly important when the protein is to be used for purposes requiring the presence of a protein with no N-terminal extension. The additional N-terminal amino acids may be removed in vitro by proteolytic cleavage by means of a suitable proteolytic enzyme, such as a trypsin-like protease, or by means of treatment with a chemical such as cyanogen bromide. It may also be possible to effect cleavage at the additional processing site by the host yeast organism, selecting a processing site specific for another yeast proteolytic enzyme.

For some purposes, however, it may be advantageous to design the N-terminal extension to fit a specific purpose. Thus, the extension may serve as a marker for detection of the protein, as an aid to purify the protein or as a means to control the action of a pharmaceutical in vivo, e.g. to prolong the half-life of a drug or to target it to a specific location in the body.

In a preferred embodiment of the polypeptide of the present invention, $X^1$ and/or $X^4$ represent an amino acid sequence of 1-4 amino acids. In this embodiment, the amino acid immediately adjacent to $X^2$ is preferably Glu or Asp, the amino acid immediately adjacent to $X^3$ is preferably Glu or Asp, or both are Glu or Asp, as this provides a favourable presentation of the processing site due to the hydrophilic nature of these amino acids, as explained in more detail above. The amino acid sequence represented by $X^1$ or $X^4$ may suitably comprise more than one Glu or Asp.

In another interesting embodiment of the polypeptide of the invention, $X^1$ and $X^4$ both represent one or more amino acids, in other words, the polypeptide is modified both at the C-terminal end of the leader peptide and at the N-terminal end of the heterologous protein In this embodiment, $X^1$ and $X^4$ may be symmetrically identical, that is, the amino acid or acids represented by $X^1$ and $X^4$ are the same extending outwards from $X^2$ and $X^3$ respectively.

The signal peptide sequence of the polypeptide of the invention may be any signal peptide which ensures an effective direction of the expressed polypeptide into the secretory pathway of the cell. The signal peptide may be a naturally occurring signal peptide or functional parts thereof, or it may be a synthetic peptide. Suitable signal peptides have been found to be the α-factor signal peptide, the signal peptide of mouse salivary amylase, a modified carboxypeptidase signal peptide or the yeast BAR1 signal peptide. The mouse salivary amylase signal sequence is described by O Hagenbüchle et al., *Nature* 289, 1981, pp. 643-646. The carboxypeptidase signal sequence is described by L. A. Valls et al., *Cell* 48, 1987, pp. 887-897. The BAR1 signal peptide is disclosed in WO 87/02670.

The leader peptide sequence of the polypeptide of the invention may be any leader peptide which is functional in directing the expressed polypeptide to the endoplasmic reticulum and further along the secretory pathway. Possible leader sequences which are suited for this purpose are natural leader peptides derived from yeast or other organisms, such as the the α-factor leader or a functional analogue thereof. The leader peptide may also be a synthetic leader peptide, e.g. one of the synthetic leaders disclosed in International Patent Application, Publication No. WO 89/02463 U.S. Pat. No. 5,162,498 with the following amino acid sequences A. Ala-Pro-Val-Thr-Gly-Asp-Glu-Ser-Ser-Val-Glu-Ile-Pro-Glu-Glu-Ser-Leu-Ile-Gly-Phe-Leu-Asp-Leu-Ala-Gly-Glu-Glu-Ile-Ala-Glu-Asn-Thr-Thr-Leu-Ala B. Ala-Pro-Val-Thr-Gly-Asp-Glu-Ser-Ser-Val-Glu-Ile-Pro-Glu-Glu-Ser-Leu-Ile-Ile-Ala-Glu-Asn-Thr-Thr-Leu-Ala C. Ala-Pro-Val-Thr-Gly-Asp-Glu-Ser-Ser-Val-Glu-Ile-Pro-Ile-Ala-Glu-Asn-Thr-Thr-Leu-Ala- D. Ala-Pro-Val-Thr-Gly-Asp-Glu-Ser-Ser-Val-Glu-Ile-Pro-Glu-Glu-Ser-Leu-Ile-Ile-Ala-Glu-Asn-Thr-Thr-Leu-Ala-Asn-Val-Ala-Met-Ala and E. Gln-Pro-Val-Thr-Gly-Asp-Glu-Ser-Ser-Val-Glu-Ile-Pro-Glu-Glu-Ser-Leu-Ile-Ile-Ala-Glu-Asn-Thr-Thr-Leu-Ala-Asn-Val-Ala-Met-Ala or a derivative thereof.

The heterologous protein produced by the method of the invention may be any protein which may advantageously be produced in yeast. Examples of such proteins are aprotinin or other protease inhibitors, insulin (including insulin precursors), human or bovine growth hormone, interleukin, glucagon, tissue plasminogen activator, Factor VII, Factor VIII, Factor XIII, platelet-derived growth factor, enzymes, etc., or a functional analogue thereof. In the present context, the term "functional analogue" is meant to indicate a polypeptide with a similar function as the native protein (this is intended to be understood as relating to the nature rather than the level of biological activity of the native protein). The polypeptide may be structurally similar to the native protein and may be derived from the native protein by addition of one or more amino acids to either or both the C- and N-terminal end of the native protein, substitution of one or more amino acids at one or a number of different sites in the native amino acid sequence, deletion of one or more amino acids at either or both ends of the native protein or at one or several sites in the amino acid sequence, or insertion of one or more amino acids at one or more sites in the native amino acid sequence. Such modifications are well known for several of the proteins mentioned above.

According to the invention, it has surprisingly been found that modifications at the C-terminal end of the leader peptide or at the N-terminal end of the heterologous protein as described above allow for the production in high yields of correctly processed aprotinin (or a functional analogue thereof, as defined above). Aprotinin is a protease-inhibiting protein whose properties make it useful for a variety of medical purposes (e.g. in the treatment of pancreatitis, septic shock syndrome, hyperfibrinolytic haemorrhage and myocardial infarction). Administration of aprotinin in high doses significantly reduces blood loss in connection with cardiac surgery or other major surgery. Aprotinin is also useful as an additive to culture media as it inhibits host cell proteases which might otherwise cause unwanted proteolytic cleavage of expressed proteins. Difficulties have been experienced in obtaining a high yield of correctly processed aprotinin in yeast using known natural leader sequences such as the α-factor leader. Native aprotinin is initiated at the N-terminal by a basic amino acid (Arg), and for this reason the preceding processing site may be less apt for proteolytic cleavage (as explained above) when one of the known leader peptides (e.g. the α-factor leader) is employed without being modified according to the present invention, resulting in low yields, if any, of correctly processed aprotinin.

According to the present invention, particularly good results have been achieved with respect to the production of aprotinin when $X^1$ represents GluArgLeuGlu or when $X^4$ represents GluLeu or GluLeuAspLeu (cf. the following examples), although it is expected than advantageous yields of aprotinin may be obtained with other meanings of $X^1$ and $X^4$, provided that at least one amino acid, and most preferably the one closest to the processing site is a negatively charged amino acid, as explained above.

Also according to the invention, it has been found that modifications at the C-terminal end of the leader peptide or at the N-terminal end of the heterologous protein as described above permit production of high yields of correctly processed insulin precursor (or a functional analogue thereof as defined above). In this embodiment of the invention, $X^1$ may represent Glu-Arg-Leu-Glu or Lys-Glu-Leu-Glu in which case $X^4$ usually represents a peptide bond. Alternatively, $X^4$ may represent Glu in which case $X^1$ usually respresents a peptide bond. In particular, advantageous results have been achieved according to the invention with respect to the expression of the insulin analogue precursor B(1-29)-AlaAlaLys-A(1-21) when $X^1$ represents Lys-GluLeuGlu or when $X^4$ represents a substitution of Phe as the first amino acid of the insulin precursor by Glu (cf. the following examples). Reasonable yields have also been obtained of the insulin analogue precursor B(1-29) SerAspAspAlaLys-A(1-21) when $X^1$ represents Lys-Glu-Leu-Glu. Furthermore, it is expected that high yields of insulin precursor may be obtained with other meanings of $X^1$ and $X^4$, provided that at least one amino acid, and most preferably, the one closest to the processing site is a negatively charged amino acid, as explained above.

The DNA construct of the invention encoding the polypeptide of the invention may be prepared synthetically by established standard methods, e.g. the phosphoamidite method described by S. L. Beaucage and M. H. Caruthers, *Tetrahedron Letters* 22 1981, pp. 1859–1869, or the method described by Matthes et al., *EMBO Journal* 3, 1984, pp. 801–805. According to the phosphoamidite method, oligonucleotides are synthesized, e.g. in an automatic DNA synthesizer, purified, duplexed and ligated to form the synthetic DNA construct.

The DNA construct of the invention may also be of genomic or cDNA origin, for instance obtained by preparing a genomic or cDNA library and screening for DNA sequences coding for all or part of the polypeptide of the invention by hybridization using synthetic oligonucleotide probes in accordance with standard techniques (cf. T. Maniatis et al., *Molecular Cloning: A Laboratory Manual*, Cold Spring Harbor, 1982). In this case, a genomic or cDNA sequence encoding a signal and leader peptide may be joined to a genomic or cDNA sequence encoding the heterologous protein, after which the DNA sequence may be modified at a site corresponding to the amino acid sequence $X^1$-$X^2$-$X^3$-$X^4$ of the polypeptide, e.g. by site-directed mutagenesis using synthetic oligonucleotides encoding the desired amino acid sequence for homologous recombination in accordance with well-known procedures.

Finally, the DNA construct may be of mixed synthetic and genomic, mixed synthetic and cDNA or mixed genomic and cDNA origin prepared by annealing fragments of synthetic, genomic or cDNA origin (as appropriate), the fragments corresponding to various parts of the entire DNA construct, in accordance with standard techniques. Thus, it may be envisaged that the DNA sequence encoding the heterologous protein may be of genomic origin, while the sequence encoding the leader peptide may be prepared synthetically.

Preferred DNA constructs encoding aprotinin are as shown in the appended FIGS. 4, 7, 9, 11 and 12, or suitable modifications thereof coding for aprotinin or a functional analogue thereof. Examples of suitable modifications of the DNA sequence are nucleotide substitutions which do not give rise to another amino acid sequence of the protein, but which may correspond to the codon usage of the yeast organism into which the DNA construct is inserted or nucleotide substitutions which do give rise to a different amino acid sequence and therefore, possibly, a different protein structure without, however, impairing the anti-protease properties of native aprotinin. Other examples of possible modifications are insertion of one or more nucleotides into the sequence, addition of one or more nucleotides at either end of the sequence and deletion of one or more nucleotides at either end of or within the sequence. Examples of specific aprotinin analogues are those described in European Patent Application, Publication No. 339 942.

Preferred DNA constructs encoding insulin precursors are as shown in the appended FIGS. 16 and 17 or suitable modifications thereof, as defined above.

The recombinant expression vector carrying a DNA sequence encoding the polypeptide of the invention may be any vector which is capable of replicating in yeast organisms. In the vector, the DNA sequence encoding the polypeptide of the invention should be operably connected to a suitable promoter sequence. The promoter may be any DNA sequence which shows transcriptional activity in yeast and may be derived from genes encoding proteins either homologous or heterologous to yeast. The promoter is preferably derived from a gene encoding a protein homologous to yeast. Examples of suitable promoters are the *Saccharomyces cerevisiae* Mα1, TPI, ADH or PGK promoters.

The DNA sequence encoding the polypeptide of the invention should also be operably connected to a suitable terminator, e.g. the TPI terminator (cf. T. Alber and G. Kawasaki, *J. Mol. Appl. Genet.* 1, 1982, pp. 419–434).

The recombinant expression vector of the invention further comprises a DNA sequence enabling the vector to replicate in yeast. Examples of such sequences are the yeast plasmid 2μ replication genes REP 1-3 and origin of replication. The vector may also comprise a selectable marker, e.g. the *Schizosaccharomyces pombe* TPI gene as described by P. R. Russell, *Gene* 40, 1985, pp. 125–130.

The procedures used to ligate the DNA sequences coding for the polypeptide of the invention, the promoter and the terminator, respectively, and to insert them into suitable yeast vectors containing the information necessary for yeast replication, are well known to persons skilled in the art (cf., for instance, Maniatis et al., op.cit.). It will be understood that the vector may be constructed either by first preparing a DNA construct containing the entire DNA sequence coding for the polypeptide of the invention and subsequently inserting this fragment into a suitable expression vector, or by sequentially inserting DNA fragments containing genetic information for the individual elements (such as the signal, leader or heterologous protein) followed by ligation.

The yeast organism used in the process of the invention may be any suitable yeast organism which, on cultivation, produces large amounts of the heterologous protein or polypeptide in question. Examples of suitable yeast organisms may be strains of the yeast species *Saccharomyces cerevisiae, Saccharomyces kluyveri, Schizosaccharomyces pombe* or *Saccharomyces uvarum*. The transformation of the yeast cells may for instance be effected by protoplast formation (cf. Example 1 below) followed by transformation in a manner known per se. The medium used to cultivate the cells may be any conventional medium suitable for growing yeast organisms. The secreted heterologous protein, a significant proportion of which will be present in the medium in correctly processed form, may be recovered from the medium by conventional procedures including separating the yeast cells from the medium by centrifugation or filtration, precipitating the proteinaceous components of the supernatant or filtrate by means of a salt, e.g. ammonium sulphate, followed by purification by a variety of chromatographic procedures, e.g. ion exchange chromatography, affinity chromatography, or the like.

In an additional aspect, the invention relates to a novel aprotinin analogue of the general formula $X^4$-aprotinin(1-58), wherein $X^4$ represents an N-terminal extension by one or more amino acids at least one of which is a negatively charged amino acid selected from the group consisting of Glu and Asp. $X^4$ may represent a sequence of 1-6 amino acids, in particular 1-4 amino acids, and may have any of the meanings given above. Particularly preferred meanings of $X^4$ are Glu-Leu and Glu-Leu-Asp-Leu.

BRIEF DESCRIPTION OF THE DRAWINGS

The invention is further disclosed in the following examples with reference to the appended drawings, wherein FIG. 1 shows the DNA and amino acid sequence of aprotinin(1-58). The staggered lines shown in the DNA sequence denote sites at which duplexes formed from synthetic oligonucleotides were ligated.

FIG. 4 shows the DNA sequence of a 406 bp EcoRI-XbaI fragment from pKFN-849 and pKFN-855. The arrow denotes the site at which proteolytic cleavage takes place during secretion.

FIG. 7 shows the DNA sequence of a 412 bp EcoRI-XbaI fragment from pKFN-852 and pKFN-858. The arrow denotes the site at which proteolytic cleavage takes place during secretion.

FIG. 9 shows the DNA sequence of a 412 bp EcoRI-XbaI fragment from pKFN-995 and pKFN-998. The arrow denotes the site of proteolytic cleavage during secretion.

FIG. 11 shows the DNA sequence of the 412 bp EcoRI-XbaI fragment from pKFN-1000 and pKFN-1003. The arrow denotes the site at which proteolytic cleavage takes place during secretion.

FIG. 12 shows the DNA sequence of a synthetic aprotinin(3-58) gene. The staggered lines within the sequence indicate the sites where five duplexes formed from 10 synthesized oligonucleotides are ligated.

FIG. 16 shows the DNA sequence of the modified leader-insulin precursor gene from pLaC-240.

FIG. 17 shows the DNA sequence of a 508 bp EcoRI-XbaI fragment from pKFN-458 encoding the MFα1-signal-leader(1-85) and insulin analogue precursor B(1-29,1Glu+27Glu)-AlaAlaLys-A(1-21).

EXAMPLES

Example 1

Production of Glu-Leu-Aprotinin(1-58) from yeast strain KFN-837)

a) Construction of plasmid pKFN-802

A synthetic gene coding for aprotinin(1-58) was constructed from 10 oligonucleotides by ligation.

The oligonucleotides were synthesized on an automatic DNA synthesizer using phosphoramidite chemistry on a controlled pore glass support (Beaucage, S. L., and Caruthers, M. H., *Tetrahedron Letters* 22, (1981) 1859–1869).

The following 10 oligonucleotides were synthesized:
NOR-760: CATGGCCAAAAGAAGGCCT-GATTTCTGTTTGGAACCT-CCATACACTGGTCC
NOR-754: TTACATGGACCAGTGTATG-GAGGTTCCAAACAGAAAT-CAGGCCTTCTTTTGGC
NOR-354: ATGTAAAGCTAGAATCAT-CAGATACTTCTACAACG
NOR-355: CTTGGCGTTGTAGAAGTATCTGAT-GATTCTAGCT NOR-356: CCAAGGCTGGTTTGTGT-CAAACTTTCGTTTACGGTGGCT
NOR-357: CTCTGCAGCCACCGTAAAC-GAAAGTTTGACACAAACCAGC
NOR-358: GCAGAGCTAAGAGAAACAACTT-CAAGT
NOR-359: AGCAGACTTGAAGTTGTTTCTCT-TAG
NOR-360: CTGCTGAAGACTGCAT-GAGAACTTGTGGTGGTGCCTAAT
NOR-361: CTAGATTAGGCACCAC-CACAAGTTCTCATGCAGTCTTC 5 duplexes A–E were formed from the above 10 oligonucleotides as shown in FIG. 1.

20 pmole of each of the duplexes A–E were formed from the corresponding pairs of 5'-phosphorylated oligonucleotides by heating for 5 min. at 90° C. followed by cooling to room temperature over a period of 75 minutes. The five duplexes were mixed and treated with T4 DNA ligase. The synthetic gene was isolated as a 191 bp band after electrophoresis of the ligation mixture on a 2% agarose gel. The obtained synthetic gene is shown in FIG. 1.

The synthetic gene was ligated to a 209 bp EcoRI-NcoI fragment from pLaC212spx3 and to the 2.7 kb EcoRI-XbaI fragment of plasmid pUC19 (Yanisch-Perron, C., Vieira, J. and Messing, J., Gene 33 (1985), 103–119). Plasmid pLaC212spx3 is described in Example 3 of International Patent Application, Publication No. WO 89/02463.

The 209 bp EcoRI-NcoI fragment from pLaC212spx3 encodes a synthetic yeast leader peptide.

The ligation mixture was used to transform a competent E. coli strain r−, m+) selecting for ampicillin resistance. Sequencing of a $^{32}$p-XbaI-EcoRI fragment (Maxam, A. and Gilbert, W., Methods Enzymol. 65 (1980), 499–560) showed that plasmids from the resulting colonies contained the correct DNA sequence for aprotinin(1-58).

Figure 2:
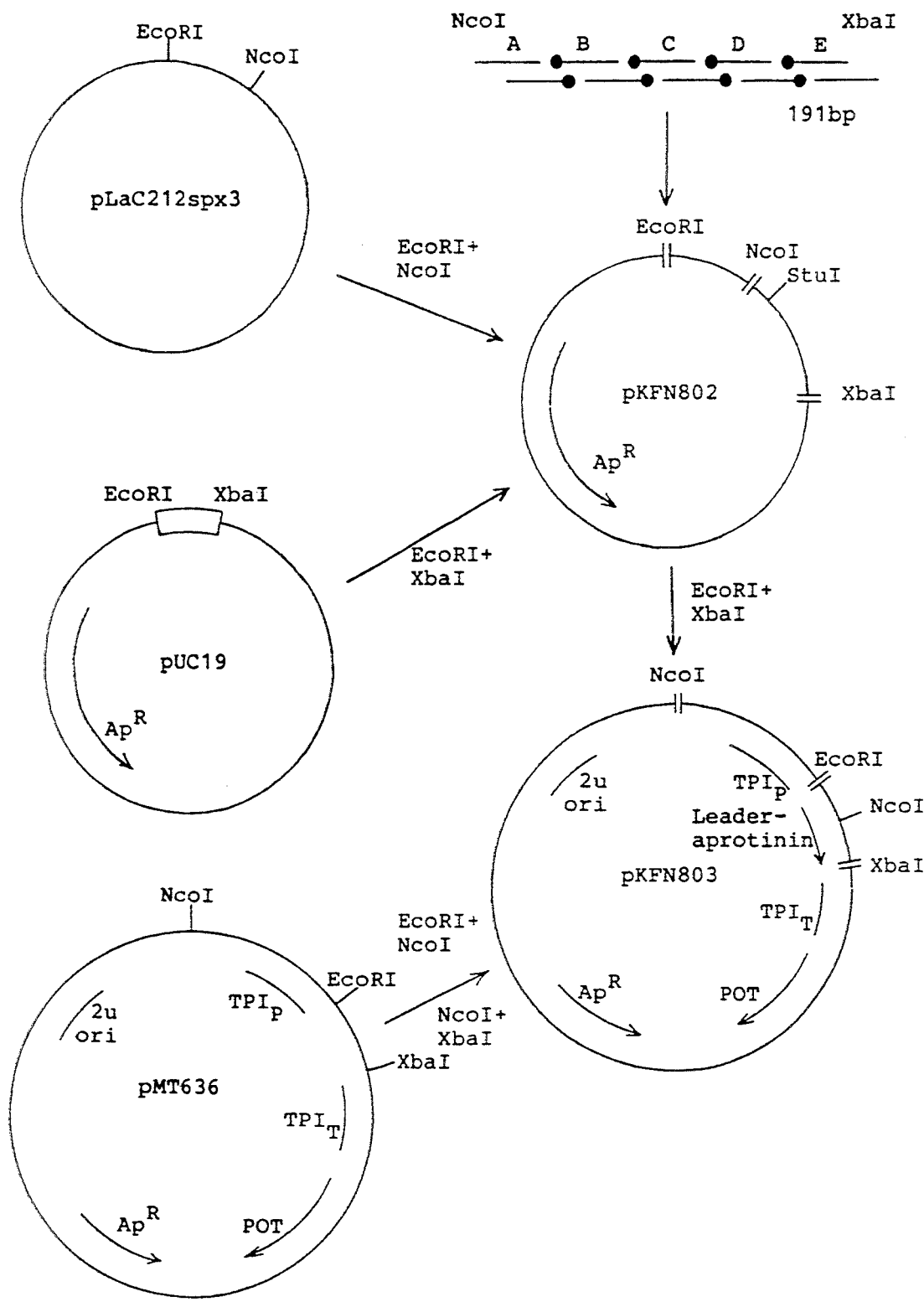
FIG. 2 shows the construction of plasmid pKFN-802 and pKFN-803.

One plasmid pKFN802 was selected for further use. The construction of plasmid pKFN802 is illustrated in FIG. 2.

b) Construction of plasmids pKFN-849, pKFN-855 and yeast strain KFN-837.

The 3.0 kb NcoI-StuI fragment of pKFN-802 was ligated to the synthetic fragment NOR-790/791 with T4 DNA ligase:

```
        M   A   K   R   E   L   R

CATGGCTAAGAGAGAATTGAGA
            CGATTCTCTCTTAACTCT
```

Figure 3:
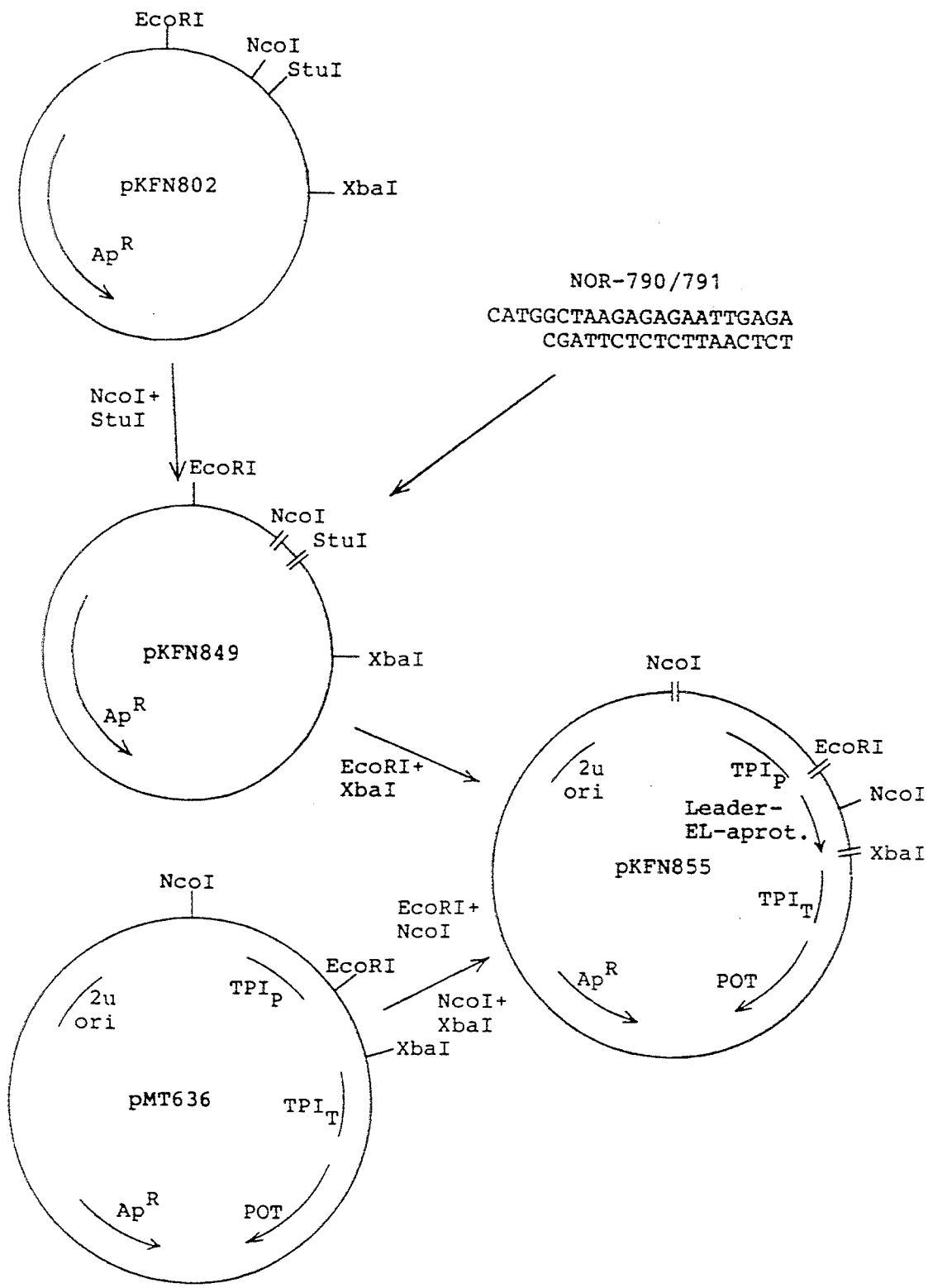
FIG. 3 shows the construction of plasmid pKFN-849 and pKFN-855.

The ligation mixture was digested with the restriction enzyme StuI in order to reduce any background of pKFN-802, and the resulting mixture was used to transform a competent E. coli strain (r−, m+) selecting for ampicillin resistance. Plasmid pKFN-849 from one of the resulting colonies was shown by DNA sequencing (Sanger, F., Micklen, S., and Coulson, A. R., Proc. Natl. Acad. Sci. USA 74 (1977), 5463–5467) to contain the DNA sequence for Glu-Leu-Aprotinin(1-58) correctly fused to the synthetic yeast leader gene. The construction of plasmid pKFN-849 is illustrated in FIG. 3.

pKFN-849 was cut with EcoRI and XbaI and the 406 bp fragment was ligated to the 9.5 kb NcoI-XbaI fragment from pMT636 and the 1.4 kb NcoI-EcoRI fragment from pMT636, resulting in plasmid pKFN-855, see FIG. 3. Plasmid pMT636 is described in International Patent Application No. PCT/DK88/00138.

pMT636 is an E. coli - S. cerevisiae shuttle vector containing the Schizosaccharomyces pombe TPI gene (POT) (Russell, P. R., Gene 40 (1985), 125-130), the S. cerevisiae triosephosphate isomerase promoter and terminator, $TPI_p$ and $TPI_T$ (Alber, T., and Kawasaki, G. J.Mol.Appl.Gen. 1 (1982), 419-434). Plasmid pKFN-855 contains the following sequence:

$TPI_p$-LaC212spx3 signal-leader-Glu-Leu-aprotinin(1-58)-$TPI_T$ where LaC212spx3 signal-leader is the synthetic yeast leader described in International Patent Application, Publication No. WO 89/02463. The DNA sequence of the 406 bp EcoRI-XbaI fragment from pKFN-849 and pKFN-855 is shown in FIG. 4.

S. cerevisiae strain MT663 (E2-7B XE11-36 a/α, Δtpi Δtpi, pep 4-3/pep 4-3) was grown on YPGaL (1% Bacto yeast extract, 2% Bacto peptone, 2% galactose, 1% lactate) to an O.D. at 600 nm of 0.6.

100 ml of culture was harvested by centrifugation, washed with 10 ml of water, recentrifugated and resuspended in 10 ml of a solution containing 1.2M sorbitol, 25 mM Na$_2$EDTA pH=8.0 and 6.7 mg/ml dithiothreitol. The suspension was incubated at 30° C. for 15 minutes, centrifuged and the cells resuspended in 10 ml of a solution containing 1.2M sorbitol, 10 mM Na$_2$EDTA, 0.1M sodium citrate, pH=5.8, and 2 mg Novozym($^R$) 234. The suspension was incubated at 30° C. for 30 minutes, the cells collected by centrifugation, washed in 10 ml of 1.2M sorbitol and 10 ml of CAS (1.2M sorbitol, 10 mM CaCl$_2$, 10 mM Tris HCl (Tris=-Tris(hydroxymethyl)aminomethane) pH=7.5) and resuspended in 2 ml of CAS. For transformation 0.1 ml of CAS-resuspended cells were mixed with approx. 1 µg of plasmid pKFN-855 and left at room temperature for 15 minutes. 1 ml of (20% polyethylene glycol 4000, 20 mM CaCl$_2$, 10 mM CaCl$_2$, 10 mM Tris HCl, pH=7.5) was added and the mixture left for a further 30 minutes at room temperature. The mixture was centrifuged and the pellet resuspended in 0.1 ml of SOS (1.2M sorbitol, 33% v/v YPD, 6.7 mM CaCl$_2$, 14 µg/ml leucine) and incubated at 30° C. for 2 hours. The suspension was then centrifuged and the pellet resuspended in 0.5 ml of 1.2M sorbitol. Then, 6 ml of top agar (the SC medium of Sherman et al., (Methods in Yeast Genetics, Cold Spring Harbor Laboratory (1981)) containing 1.2M sorbitol plus 2.5% agar) at 52° C. was added and the suspension poured on top of plates containing the same agar-solidified, sorbitol containing medium. Transformant colonies were picked after 3 days at 30° C., reisolated and used to start liquid cultures. One such transformant KFN-837 was selected for further characterization.

Yeast strain KFN-837 was grown on YPD medium (1% yeast extract, 2% peptone (from Difco Laboratories), and 6% glucose). A 200 ml culture of the strain was shaken at 250 rpm at 30° C. for 3 days to an O.D. at 600 nm of 20 (Dry yeast biomass 18.8 g/liter). After centrifugation the supernatant was analyzed by FPLC ion exchange chromatography. The yeast supernatant was filtered through a 0.22 µm Millex GV filter unit and 1 ml was applied on a MonoS cation exchange column (0.5×5 cm) equilibrated with 20 mM Bicine, pH=8.7. After wash with equilibration buffer the column was eluted with a linear NaCl gradient (0–1M) in equilibration buffer. Trypsin inhibitor activity was quantified in the eluted fractions by spectrophotometric assay (Kassel, B., *Methods Enzymol.* 19 (1970), 844–852) and furthermore by integration of absorption at 280 nm from $$E^{1\%}_{280}(aprotinin) = 8.3$$

The yield was 120 rag/liter of Glu-Leu-aprotinin(1-58).

For amino acid analysis and N-terminal sequencing concentration and further purification of the gradient eluted (Glu-Leu-aprotinin (1-58) was accomplished by HPLC on a reversed phase column (Vydac C4, 4.6×250 mm). Elution was carried out with a CH₃CN gradient in 0.1% TFA. The collected fractions were concentrated to about 100 μl by vacuum centrifugation and samples were taken for N-terminal sequencing and amino acid analysis.

By N-terminal sequencing the following sequence was found:

Glu-Leu-Arg-Pro-Asp-Phe-X-Leu-Glu-pro-pro-Tyr-Thr-Gly-pro-X-Lys-Ala-Arg-Ile-Ile-Arg-Tyr-Phe-Tyr-Asn-Ala-Lys-Ala confirming that the N-terminal end is correct. Half-cysteine residues are not determined by this method, which is in accordance with the blank cycles (X) obtained for residues No. 7 and 16.

The amino acid analysis is shown in Table 1. From this table it appears that the product has the expected amino acid composition, i.e. more Glu and Leu. The slightly lowered content of Ile can most probably be ascribed to incomplete hydrolysis of Ile(18)-Ile(19) (this is well known in the art). Also, Arg is slightly higher than expected. This is, however, also seen with native aprotinin (Table 1, third column).

When compared by the above-mentioned method of Kassel the specific activity of Glu-Leu-aprotinin(1-58) was found to be identical within the experimental error with the specific activity of native aprotinin. The trypsin and plasmin inhibition by Glu-Leu-aprotinin (1-58) in terms of titration curves determined as described below were indistinguishable from that of bovine pancreatic aprotinin (Aprotinin Novo). After incubation of the enzyme with aprotinin or its analogues for 30 minutes, 0.6 mM S 2251 (KabiVitrum) was added and the activity measured as the rate of nitroaniline production. The activity as a function of aprotinin concentration is plotted in FIG. 5A and 5B. Complete inhibition of both enzymes with all three inhibitors was observed.

Example 2

Production of Glu-Leu-Asp-Leu-aprotinin(1-58) from yeast strain KFN-840

A synthetic gene encoding Glu-Leu-Asp-Leu-aprotinin(1-58) was constructed as described in Example 1. The synthetic fragment NOR-793/794 was used instead of NOR-790/791:

```
        M   A   K   R   E   L   D   L   R
        CATGGCTAAGAGAGAATTGGACTTGAGA
            CGATTCTCTCTTAACCTGAACTCT
```

The pUC19 derived plasmid pKFN-852 was constructed in a similar way as pKFN-849.

By following the procedure of Example 1 a plasmid pKFN-858 was obtained containing the following construction TPI$_p$-LaC212spx3 signal-leader-GluLeuAspLeu-aprotinin(1-58)-TPI$_T$.

Figure 6:
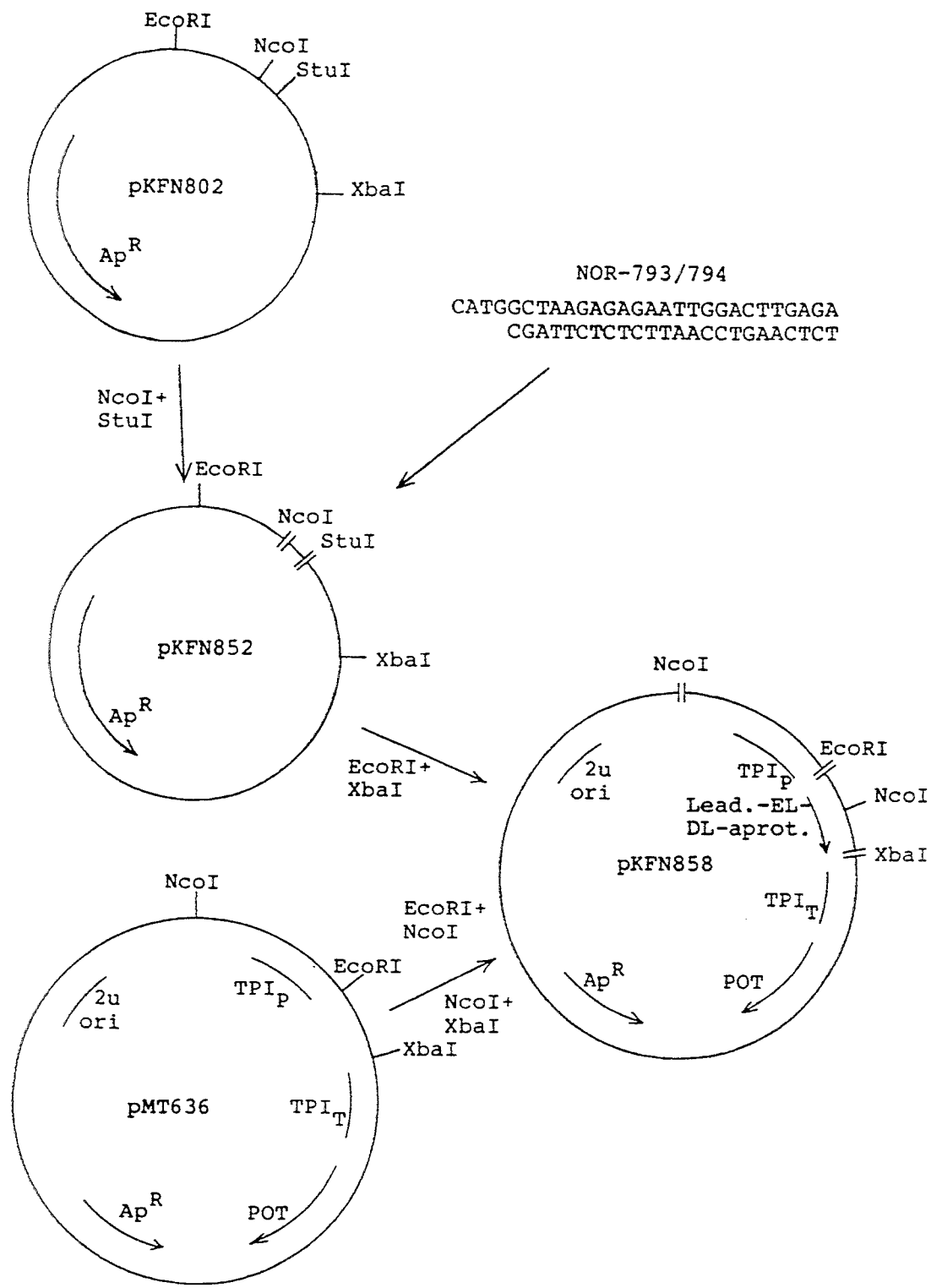
FIG. 6 shows the construction of plasmids pKFN-852 and pKFN-858.

The construction of plasmids pKFN-852 and pKFN-858 is illustrated in FIG. 6. The DNA sequence of the 412 bp EcoRI-XbaI fragment from pKFN-852 and pKFN-858 is given in FIG. 7.

Plasmid pKFN-858 was transformed into yeast strain MT663 as described above resulting in yeast strain KFN-840.

A 200 ml culture of KFN-840 in YPD medium was shaken at 250 rpm at 30° C. for 3 days to an O.D. at 600 mn of 18 (dry biomass 16.7 mg/liter). FPLC ion chromatography of the supernatant as described above gave a yield of 90 mg/liter of Glu-Leu-Asp-Leu-aprotinin(1-58 ).

The amino acid analysis appears from table 1 and confirms the expected amino acid composition.

Figure 5A:
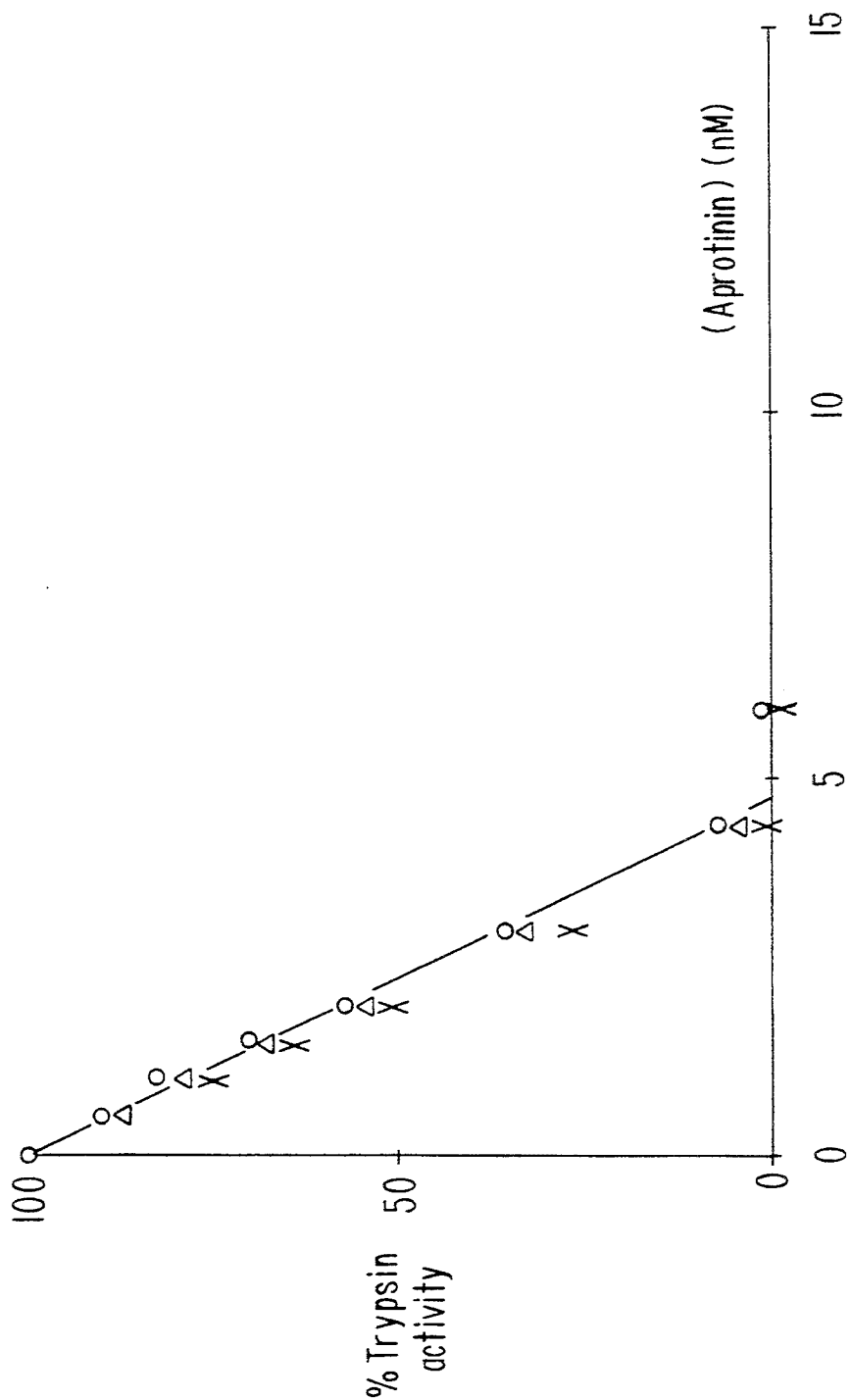
FIG. 5A and 5B show the inhibition of trypsin and plasmin, respectively, by aprotinin;   denotes bovine pancreatic aprotinin, X denotes GluLeu-aprotinin and Δ denotes GluLeuAspLeu-aprotinin.
Figure 5B:
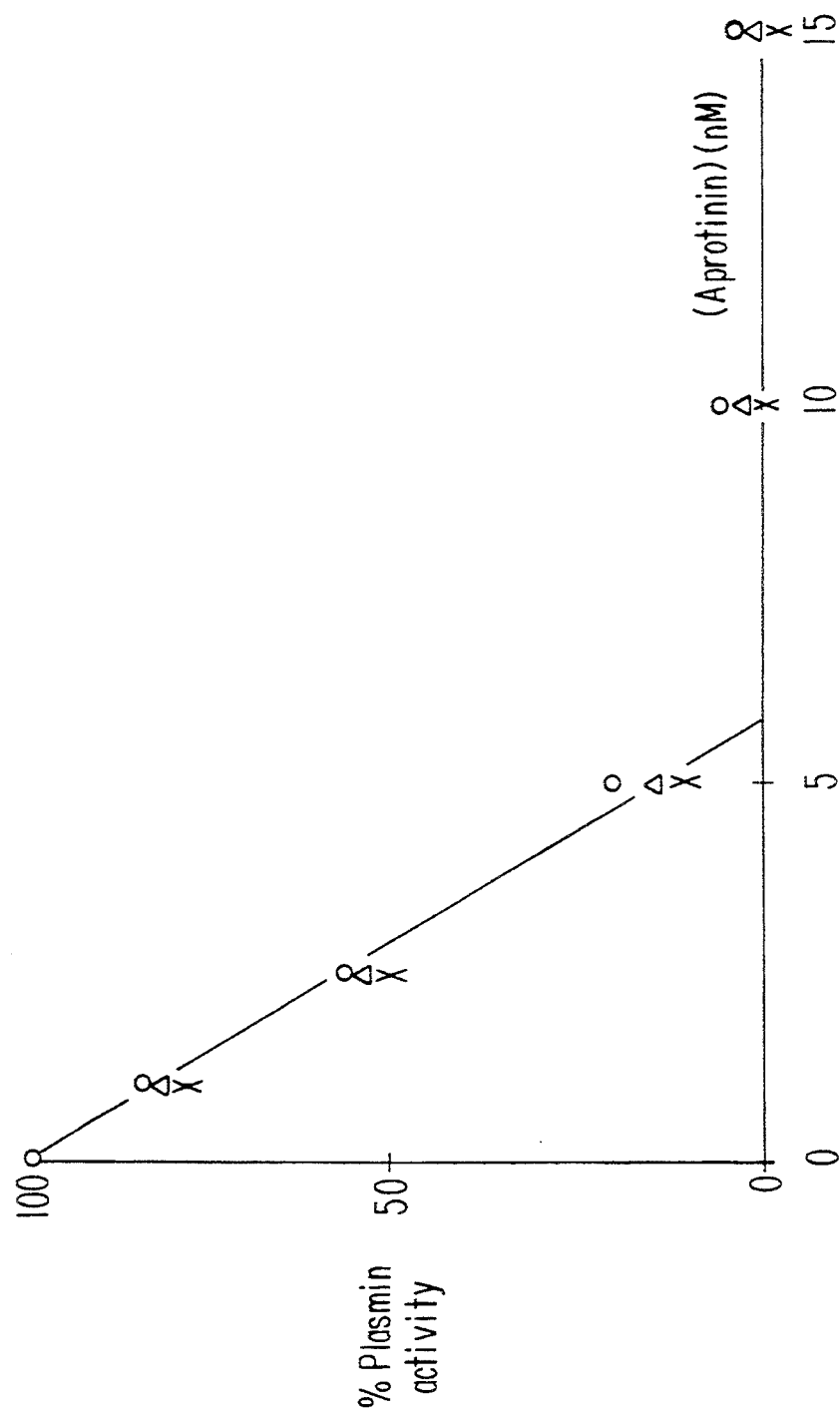

The trypsin and plasmin inhibition titration curves of Glu-Leu-Asp-Leu-aprotinin(1-58 ) were indistinguishable from that of bovine pancreatic aprotinin (Aprotinin Novo) see FIG. 5A and 5B.

Example 3

Production of aprotinin(1-5.) from yeast strain KFN-1006

Plasmid pKFN-995 was constructed from pKFN-802 by ligation of the 3.0 kb NcoI-StuI fragment to the synthetic fragment NOR-848/849:

```
        M   A   K   E   L   E   K   R   R
        CATGGCTAAGGAATTGGAGAAGAGAAGG
            CGATTCCTTAACCTCTTCTCTTCC
```

The ligation mixture was digested with the restriction enzyme BalI in order to reduce any background of pKFN-802.

Figure 8:
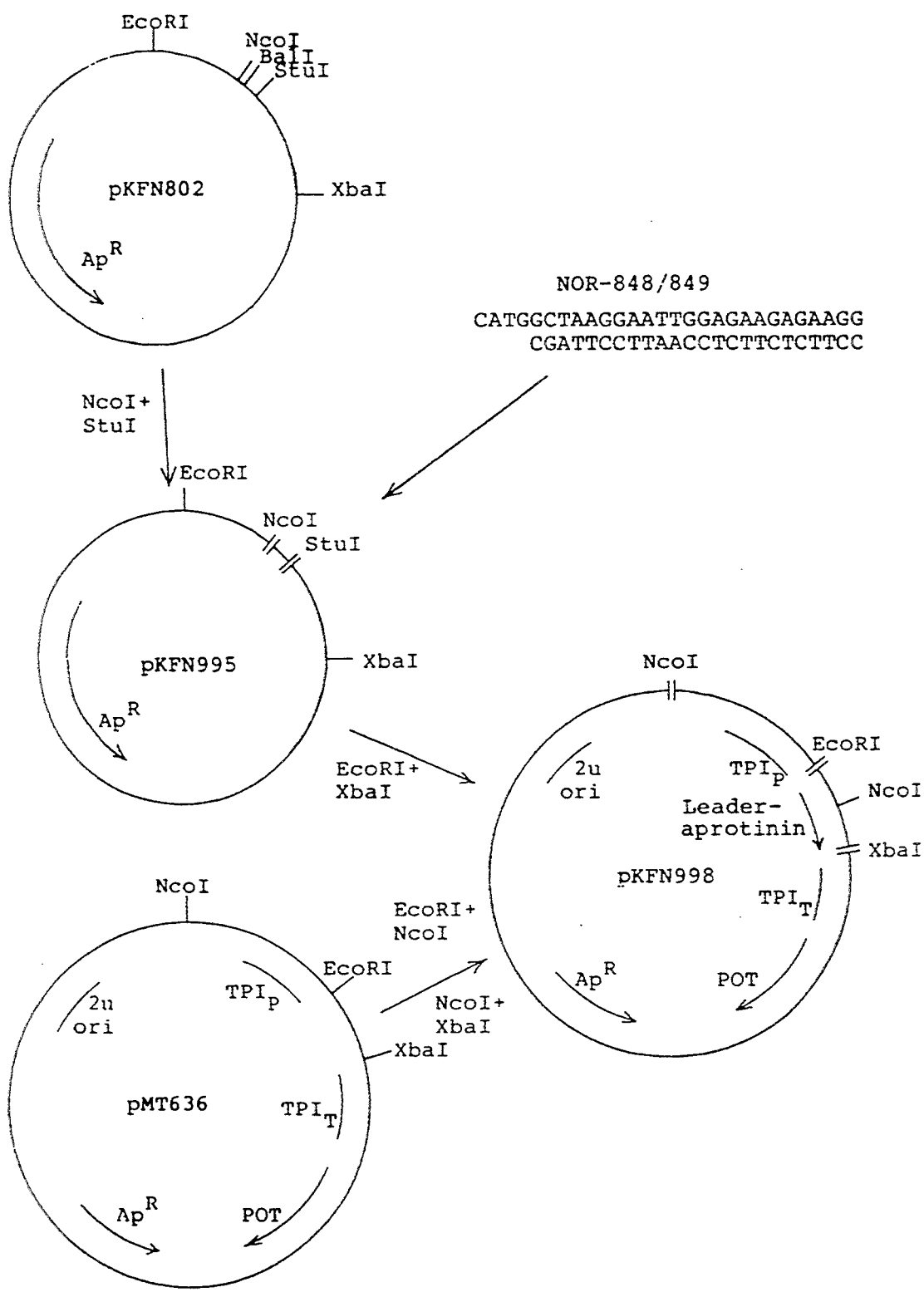
FIG. 8 shows the construction of plasmid pKFN-995 and pKFN-998.

The yeast expression plasmid pKFN-998 was constructed substantially as described in Example 1 and as shown in FIG. 8:

TPI$_p$-LaC212spx3 signal-leader(1-47) Lys-Glu-Leu-Glu Lys-Arg-aprotinin( 1-58 )-TPI$_T$ The DNA sequence of the 412 bp EcoRI-XbaI fragment from pKFN-995 and pKFN-998 is given in FIG. 9.

Plasmid pKFN-998 was transformed into yeast strain MT663 as described in Example 1 resulting in yeast strain KFN-1006. Culturing of the transformed strain KFN-1006 in YPD-medium and analysis for aprotinin(1-58) in the supernatant was performed as described above.

The yield was 30 mg/liter of aprotinin(1-58).

The amino acid analysis of the purified material confirmed the expected amino acid composition.

Example 4

Production of aprotinin(1-58) from yeast strain KFN-1008

The pUC-derived plasmid pKFN-1000 was constructed as described in Example 1 by ligation of the 3.0 kb NcoI-StuI fragment of pKFN-802 to the synthetic fragment NOR-850/851:

```
        M   A   E   R   L   E   K   R   R
        CATGGCTGAGAGATTGGAGAAGAGAAGG
            CGACTCTCTAACCTCTTCTCTTCC
```

By following the procedure of Examples 1 and 3 a yeast expression plasmid pKFN-1003 was obtained containing the following construction TPI$_p$-LaC212spx3 signal-leader(1-47)-GluArgLeuGlu Lys-Arg-aprotinin(1-58 )-TPI$_T$.

Figure 10:
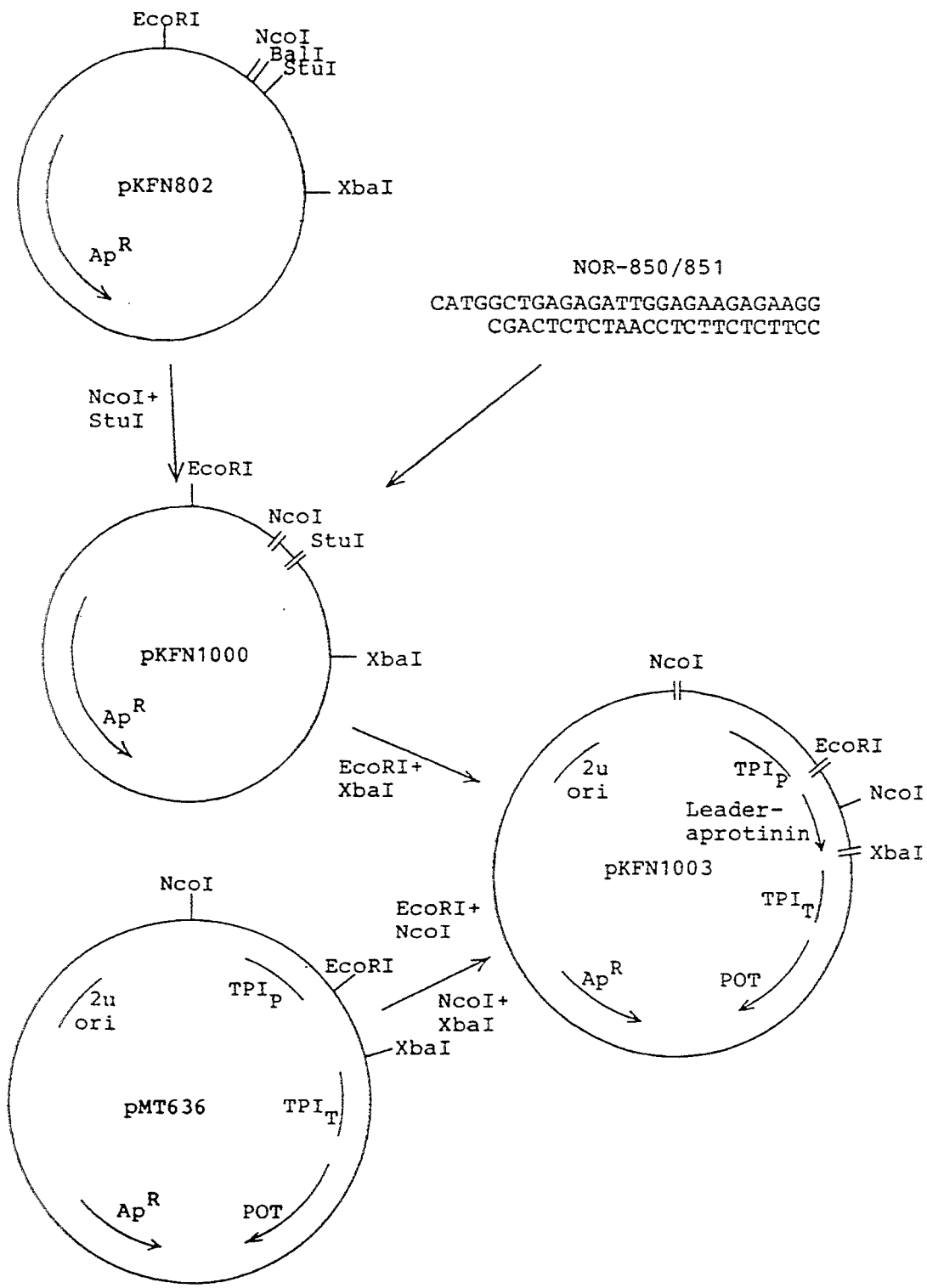
FIG. 10 shows the construction of plasmids pKFN-1000 and pKFN-1003.

The construction of plasmids pKFN-1000 and pKFN-1003 is illustrated in FIG. 10. The DNA sequence of the 412 bp EcoRIXbaI fragment from pKFN-1000 and pKFN-1003 is given in FIG. 11.

Plasmid pKFN-1003 was transformed in yeast strain MT663 as described above resulting in yeast strain KFN-1008.

Culturing of the transformed strain KFN-1008 in YPD-medium and analysis for aprotinin(1-58) in the supernatant was performed as described above. The yield was 120 mg/liter of aprotinin(1-58).

The amino acid analysis of purified material confirmed the expected amino acid composition. In addition, confirmation of the complete primary structure was obtained by gas phase sequencing of the reduced, pyridylethylated polypeptide.

Furthermore the specific inhibitory activity of the recombinant aprotinin(1-58) against trypsin was indistinguishable from that of bovine pancreatic aprotinin.

Example 5

Production of aprotinin(1-58) from yeast strain KFN-783

Plasmid pKFN-802 (cf. Example 1) was cut with EcoRI and XbaI and the 400 bp fragment was ligated to the 9.5 kb NcoI-XbaI fragment from pMT636 and the 1.4 kb NcoI-EcoRI fragment from pMT636, resulting in plasmid pKFN-803, see FIG. 2. pKFN-803 contains the following construction:

TPI$_p$-LaC212spx3 signal-leader-aprotinin(1-58)-TPI$_T$

Plasmid pKFN-803 was transformed in yeast strain MT663 as described above. Culturing of the transformed strain KFN-783 in YPD medium and FPLC ion chromatography of the supernatant was performed as described above. Aprotinin(1-58) was quantified by comparison to chromatography of a standardized solution of authentic aprotinin purified from bovine pancreas. The yield of aprotinin(1-58) was below 1 mg/liter.

TABLE 1

| Amino Acid | Aprotinin Theoretical | Aprotinin Found | KFN-837 Found | KFN-840 Found |
|---|---|---|---|---|
| Asp | 5 | 5.00 | 4.95 | 5.93 (+1) |
| Thr | 3 | 2.86 | 2.84 | 2.85 |
| Ser | 1 | 0.94 | 0.92 | 0.93 |
| Glu | 3 | 3.04 | 3.97 (+1) | 3.99 (+1) |
| Pro | 4 | 4.18 | 3.90 | 3.86 |
| Gly | 6 | 5.95 | 5.91 | 5.94 |
| Ala | 6 | 5.85 | 5.92 | 5.94 |
| Cys | 6 | 5.20 | 5.21 | 5.22 |
| Val | 1 | 0.99 | 1.00 | 1.01 |
| Met | 1 | 0.83 | 0.65 | 0.67 |
| Ile | 2 | 1.39 | 1.58 | 1.58 |
| Leu | 2 | 1.97 | 3.00 (+1) | 4.00 (+2) |
| Tyr | 4 | 3.84 | 3.74 | 3.71 |
| Phe | 4 | 3.98 | 3.94 | 3.92 |
| Lys | 4 | 3.92 | 3.99 | 3.99 |
| Arg | 6 | 6.39 | 6.35 | 6.34 |
| Totals | 58 | 56.33 | 57.87 | 59.88 |

Amino acid composition

Example 6

Production of aprotinin(3-58)

A synthetic gene for aprotinin(3-58) was constructed from a number of oligonucleotides by ligation.

The following 10 oligonucleotides were synthesized as described in Example 1:

I: AAAGAGATTTCTGTTTGGAACCTCCATACACTGGTCC 37-mer

II: TTACATGGACCAGTGTATGGAGGTTCCAAACAGAAACT 38-mer

III: ATGTAAAGCTAGAATCATCAGATACTTCTACAACG 35-mer

IV: CTTGGCGTTGTAGAAGTATCTGATGATTCTAGCT 34-mer

V: CCAAGGCTGGTTTGTGTCAAACTTTCGTTTACGGTGGCT 39-mer

VI: CTCTGCAGCCACCGTAAACGAAAGTTTGACACAAACCAGC 40-mer

VII: GCAGAGCTAAGAGAAACAACTTCAAGT 27-mer

VIII: AGCAGACTTGAAGTTGTTTCTCTTAG 26-mer

IX: CTGCTGAAGACTGCATGAGAACTTGTGGTGGTGCCTAAT 39-mer

X: CTAGATTAGGCACCACCACAAGTTCTCATGCAGTCTTC 38-mer 5 duplexes A-E were formed from the above 10 oligonucleotides as shown in FIG. 12.

20 pmole of each of the duplexes A-E was formed from the corresponding pairs of 5'-phosphorylated oligonucleotides I-X by heating for 5 min. at 90° C. followed by cooling to room temperature over a period of 75 minutes. The five duplexes were mixed and treated with T4 ligase. The synthetic gene was isolated as a 176 bp band after electrophoresis of the ligation mixture on a 2% agarose gel. The obtained synthetic gene is shown in FIG. 12.

The synthetic 176 bp gene was ligated to a 330 bp EcoRI-HgaI fragment from plasmid pKFN-9 coding for the S. cerevisiae mating factor α1 signal-leader (1-85) sequence (Markussen, J. et al., Protein-Engineering 1 (1987), 215-223) and to the 2.7 kb EcoRI-XbaI fragment from pUC19 (Yanish-Perron, C., Vieira, J. and Messing, J., Gene 93 (1985), 103-119). The construction of pKFN-9 containing a HgaI site immediately after the MFα1 leader sequence is described in EP 214 826.

The ligation mixture was used to transform a competent E. coli strain (r−, m+) selecting for ampicillin resistance. Sequencing of a $^{32}P$-XbaI-EcoRI fragment (Maxam, A. and Gilbert, W., Methods Enzymol. 65 (1980), 499-560) showed that plasmids from the resulting colonies contained the correct DNA-sequence for aprotinin(3-58).

Figure 13:
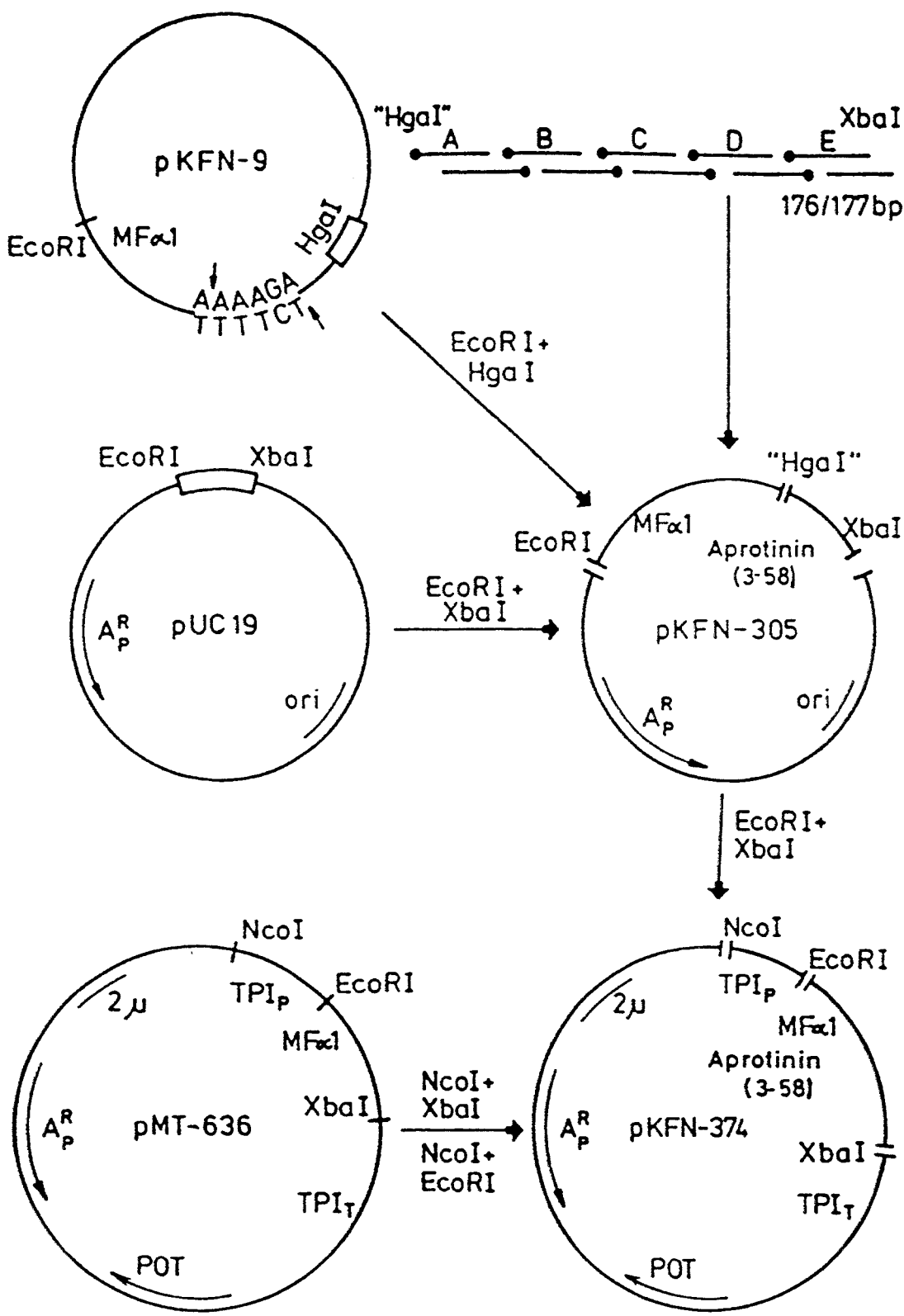
FIG. 13 shows the construction of plasmid pKFN-305 and pKFN-374/375.
Figure 14:
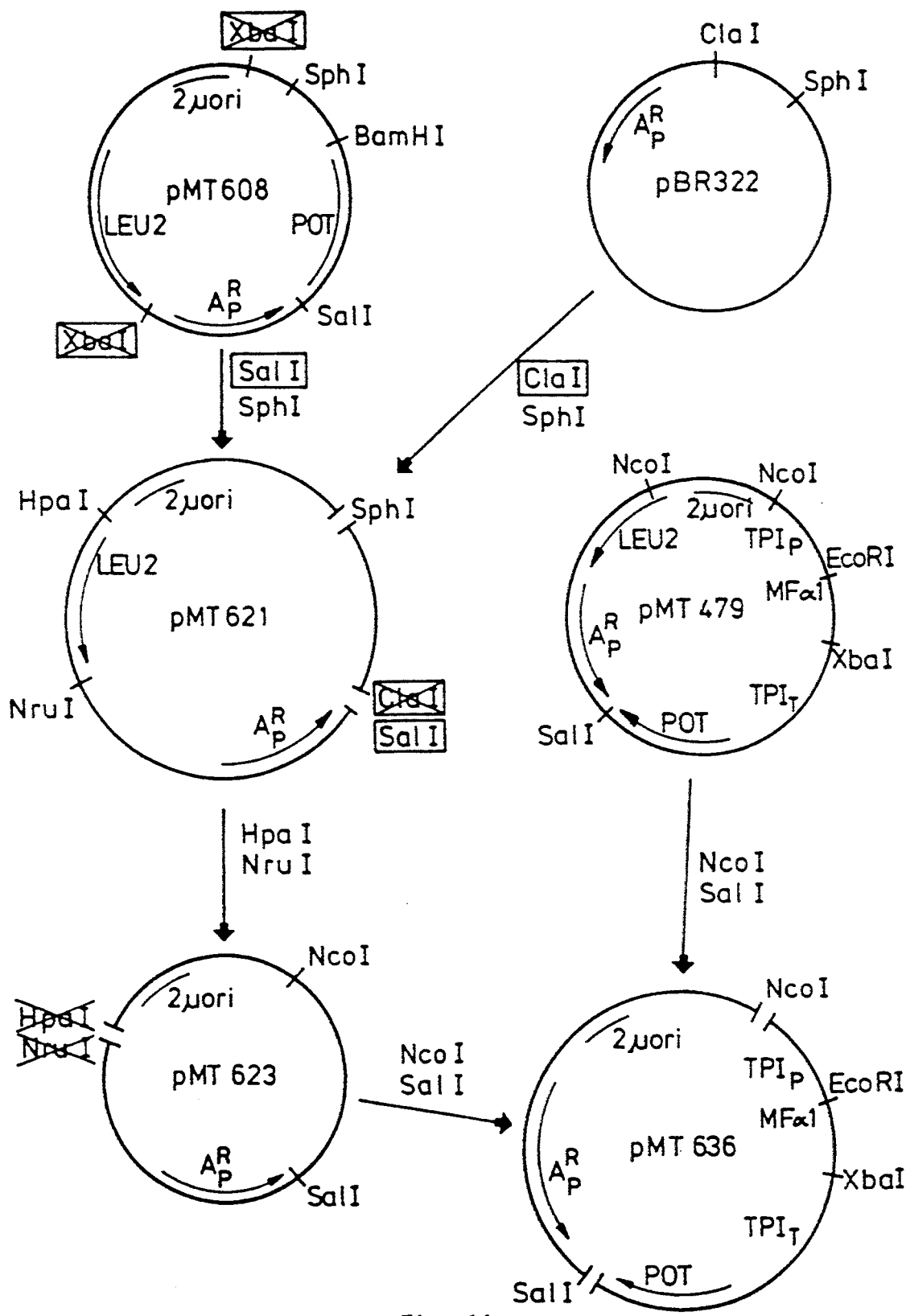
FIG. 14 shows the construction of plasmid pMT-636.

One plasmid pKNF305 was selected for further use. The construction of plasmid pKFN305 is illustrated in FIG. 13.

pKFN305 was cut with EcoRI and XbaI and the 0.5 kb fragment was ligated to the 9.5 kb NcoI-XbaI fragment from pMT636 and the 1.4 kb NcoI-EcoRI fragment from pMT636, resulting in plasmid pKFN374, see FIG. 13. Plasmid pMT636 was constructed from pMT608 after deletion of the LEU-2 gene and from pMT479, see FIG. 14. pMT608 is described in EP 195 691. pMT479 is described in EP 163 529. pMT479 contains the Schizosaccharomyces pombe TPI gene (POT), the S. cerevisiae triosephosphate isomerase promoter and terminator, $TPI_p$ and $TPI_T$ (Alber, T. and Kawasaki, G. J. Mol. Appl. Gen. 1 (1982), 419-434). Plasmid pKFN374 contains the following sequence:

$TPI_p$-MFα1-signal-leader(1-85)-aprotinin(3-58)-$TPI_T$.

where MFα1 is the S. cerevisiae mating factor alpha 1 coding sequence (Kurjan, J. and Herskowitz, I., Cell 30 (1982), 933-943), signal-leader(1-85) means that the sequence contains the first 85 amino acid residues of the MFα1 signal-leader sequence and aprotinin(3-58) is the synthetic sequence encoding an aprotinin derivative lacking the first two amino acid residues.

S. cerevisiae strain MT663 (E2-7B XE11-36 a/α, ΔtpiΔtpi, pep 4-3/pep 4-3) was grown on YPGaL (1% Bacto yeast extract, 2% Bacto peptone, 2% galactose, 1% lactate) to an O.D. at 600 nm of 0.6.

100 ml of the resulting culture was harvested by centrifugation, washed with 10 ml of water, recentrifuged and resuspended in 10 ml of a solution containing 1.2M sorbitol, 25 mM Na₂EDTA pH=8.0, and 6.7 mg/ml dithiotreitol. The suspension was incubated at 30° C. for 15 minutes, centrifuged and the cells resuspended in 10 ml of a solution containing 1.2M sorbitol, 10 mM Na₂EDTA, 0.1M sodium citrate, pH=5.8, and 2 mg Novozym ® 234. The suspension was incubated at 30° C. for 30 minutes, the cells collected by centrifugation, washed in 10 ml of 1.2M sorbitol and 10 ml of CAS (1.2M sorbitol, 10 mM CaCl₂, 10 mM Tris HCL (Tris=Tris(hydroxymethyl)amino methane) pH=7.5) and resuspended in 2 ml of CAS. For transformation 0.1 ml of CAS-resuspended cells were mixed with approximately 1 µg of plasmid pKFN374 and left at room temperature for 15 minutes. 1 ml of (20% polyethylenglycol 4000, 10 mM CaCl₁₂, 10 mM Tris HCl, pH=7.5) was added and the mixture left for further 30 minutes at room temperature. The mixture was centrifuged and the pellet resuspended in 0.1 ml of SOS (1.2M sorbitol, 33% v/v YPD, 6.7 mM CaCl₂, 14 µg/ml leucine) and incubated at 30° C. for 2 hours. The suspension was then centrifuged and the pellet resuspended in 0.5 ml of 1.2M sorbitol. Then, 6 ml of top agar (the SC medium of Sherman et al., (Methods in Yeast Genetics, Cold Spring Harbor Laboratory, 1981) containing 1.2M sorbitol plus 2.5% agar) at 52° C. was added and the suspension poured on top of plates containing the same agar-solidified, sorbitol containing medium. Transformant colonies were picked after 3 days at 30° C., reisolated and used to start liquid cultures. One such transformant KFN322 was selected for further characterization.

Yeast strain KFN322 was grown on YPD medium (1% yeast extract, 2% peptone (from Difco Laboratories), and 2% glucose). A 10 ml culture of the strain was shaken at 30° C. to an O.D. at 600 nm of 32. After centrifugation the supernatant was analyzed by FPLC ion exchange chromatography. The yeast supernatant was filtered through a 0.22 µm Millex ® GV filter unit and 1 ml was applied on a MonoS cation exchange column (0.5×5 cm) equilibrated with 20 mM Bicine, pH 8.7. After wash with equilibration buffer the column was eluted with a linear NaCl gradient (0-1M) in equilibration buffer. Trypsin inhibitor activity was quantified in the eluted fractions by spectrophotometric assay and furthermore by integration of absorption at 280 nm from $$E^{1\%}_{280}(aprotinin) = 8.3$$

The yield was about 3 mg/liter of aprotinin(3-58).

Example 7

Production of the insulin precursor B(1-29)-AlaAlaLyS-A(1-21) from yeast strain LAC1667

The 589bp SphI-NcoI and the 172bp HpaI-XbaI fragments were isolated from pLaC212spx3 (described in WO 89/02463). These fragments were joined with the synthetic adaptor

Figure 15:
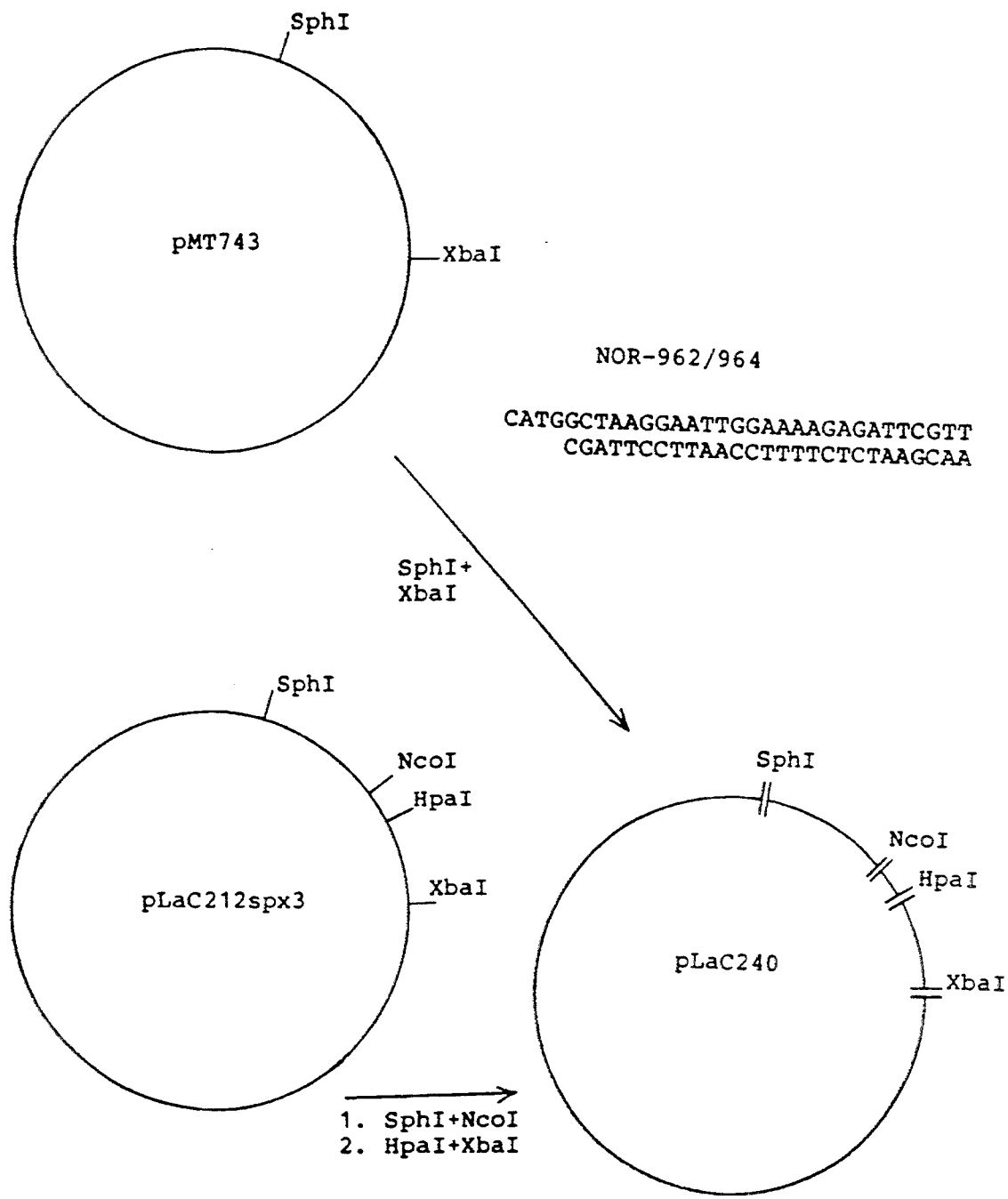
FIG. 15 shows the construction of plasmid pLaC-240.

```
           M   A   K   E   L   E   K   R   F   V
NOR-962 CATGGCTAAGGAATTGGAAAAGAGATTCGTT
NOR-964     CGATTCCTTAACCTTTTCTCTAAGCAA
``` and the 10kb XbaI-SphI fragment from pMT743 (described in WO 89/02463), resulting in the plasmid pLaC240 (see FIG. 15). The DNA sequence of the modified leader-insulin precursor gene from pLaC240 is shown in FIG. 16.

Transformation of yeast strain MT663 with plasmid pLaC240 gave rise to an insulin precursor secreting strain, LAC1667 (MT663/pLaC240), the productivity of which is 165% relative to the strain LaC1414 (MT663/pLaC212spx3) containing the gene for the unmodified leader-insulin precursor described in WO 89/02463.

Example 8

Production of insulin analogue precursor B(1-29,1Glu+27Glu)-AlaAlaLys-A(1-21) from yeast strain KFN-470

By ligation of 10 oligonucleotides a synthetic gene coding for the insulin analogue precursor B(1-29,1Glu+27Glu)-AlaAlaLys-A(1-21) was constructed. B(1-29,1Glu+27Glu) signifies the polypeptide containing the first 29 amino acid residues of the B-chain of human insulin in which Glu residues have been substituted for the B1Phe and B27Thr residues. A(1-21) is the A-chain of human insulin. A tripeptide, AlaAlaLys, connects the B29Lys residue to the A1Gly residue.

The following 10 oligonucleotides were synthesized:

NOR-542: AAAGAGAAGTTAAC-CAACACTTGTGCGGTTCCCAC
NOR-543: AACCAAGTGGGAACC-GCACAAGTGTTGGTTAACTTC
NOR-69: TTGGTTGAAGCTTT-GTACTTGGTTTGCGGTGAAAGAGGTTTCT
NOR-73: GTAGAAGAAACCTCTTTCACC-GCAAACCAAGTACAAAGCTTC
NOR-315: TCTACGAACCTAAGGCTGCTAAGG-GTATTGCT
NOR-316: ATTGTTCGACAATACCCTTAG-CAGCCTTACGTTC
NOR-70: GAACAATGCTGTACCT-CCATCTGCTCCTTGTACCAAT
NOR-71: TTTTCCAATTGGTACAAGGAG-CAGATGGAGGTACAGC
NOR-78: TGGAAAACTACTGCAACTAGACG-CAGCCCGCAGGCT
NOR-72: CTAGAGCCTGCGGGCTGCGT-CTAGTTGCAGTAG 5 duplexes were formed from the above 10 oligonucleotides and the duplexes were ligated in an similar way as described in Example 1.

The synthetic 178bp gene was ligated to the 330bp EcoRI-HgaI fragment from pKFN-9 encoding the *S. cerevisiae* mating factor alpha 1 signal-leader(i-85) sequence (Markussen, J. et al., Protein Engineering 1 (1987), 215–223) and to the 2.7 kb EcoRI-XbaI fragment of plasmid pUC19 (Yanisch-Perron, C., Vieira, J. and Messing, J., Gene 33 (1985), 103–119).

The ligation mixture was used to transform a competent *E. coli* strain r−, m+) selecting for ampicillin resistance. Sequencing of a $^{32}$P-XbaI-EcoRI fragment (Maxam, A. and Gilbert, W., Methods Enzymol. 65 (1980), 499-560) showed that plasmids from the resulting colonies contained the correct DNA sequence for the insulin analogue precursor.

One plasmid pKFN-456 was selected for further use.

By following the procedure of Example 1 a yeast expression plasmid pKFN-458 was obtained containing the following expression cassette:

TPI$_P$-MFα1-signal-leader(1-85 )-B(1-29,1Glu+27-Glu)-AlaAlaLys-A(1-21)-TPI$_T$.

The DNA sequence of the 508bp EcoRI-XbaI fragment from pKFN-456 and pKFN-458 is given in FIG. 17.

Plasmid pKFN-458 was transformed into yeast strain MT-663 as described above resulting in yeast strain KFN-470.

Culturing of the transformed strain KFN-470 in YPD medium was performed as described above. The yield of insulin analogue precursor in the supernatant was determined by HPLC as described (L. Snel et al., Chromatographia 24 (1987), 329–332).

In Table 2 the expression levels of the insulin analogue precursors B(1-29,1Glu+27Glu)-AlaAlaLys-A(1-21) and B(1-29,27Glu)-AlaAlaLys-A(1-21) and the insulin precursor B(1-29)-AlaAlaLys-A(1-21) are compared. All three precursors were expressed in the same host strain, MT-663, transformed with the S. pombe TPI gene containing plasmids with the expression cassette.

TPI$_P$-MFα1 -signal-leader(1 -85 )-precursor-TPI$_T$.

TABLE 2

Expression levels of precursors of insulin and insulin analogues in yeast transformants

| Precursor | Expression Level* |
|---|---|
| B(1-29)-AlaAlaLys-A(1-21) | 100% |
| B(1-29),27Glu)-AlaAlaLys-A(1-21) | 148% |
| B(1-29,1Glu + 27Glu)-AlaAlaLys-A(1-21) | 479% |

*The expression levels are indicated as a percentage of the expression level of the insulin precursor B(1-29)-AlaAlaLys-A(1-21), which is arbitrarily set to 100%.

We claim:

1. A polypeptide comprising a fusion of a signal peptide, a leader peptide and a heterologous protein or polypeptide, the polypeptide having the following structure:

signal peptide-leader peptide-$X^1X^2X^3X^4$-heterologous protein wherein $X^1$ is part of the leader peptide and is a peptide bond or is one or more amino acids which may be the same or different, $X^2$ and $X^3$ are the same or different and $X^2$ and $X^3$ are each a basic amino acid selected from the group consisting of Lys and Arg, $X^2$ and $X^3$ together defining a yeast processing site, and $X^4$ is part of the heterologous protein and is a peptide bond or is one or more amino acids which may be the same or different, with the proviso that $X^1$ or $X^4$ is one or more amino acids in which at least one of the amino acids of $X^1$ or $X^4$ is a negatively charged amino acid selected from the group consisting of Glu and Asp, and that when the signal and leader peptide is the MFα prepro peptide and wherein $X^1$ is a peptide bond, $X^4$ is not Glu-Ala-Glu-Ala or Glu-Ala-Glu-Ala-Ser-Leu-Asp, and that when $X^4$ is a peptide bond, $X^1$ is not Ser-Leu-Asp.

2. A polypeptide according to claim 1, wherein $X^1$ is Glu or Asp.

3. A polypeptide according to claim 1, wherein $X^1$ is a sequence of two amino acids with the structure BA, wherein A is Glu or Asp, and B is Glu, Asp, Val, Gly or Leu.

4. A polypeptide according to claim 1, wherein $X^1$ is a sequence of three amino acids with the structure CBA, wherein A is Glu or Asp; B is Glu, Asp, Val, Gly or Leu; and C is Glu, Asp, Pro, Gly, Val, Leu, Arg, or Lys.

5. A Polypeptide according to claim 1, wherein $X^1$ is a sequence of four amino acids with the structure DCBA, wherein A is Glu or Asp: B is Glu, Asp, Val, Gly or Leu; C is Glu, Asp, Pro, Gly, Val, Leu, Arg, or Lys; and D is Glu, Asp, Pro, Gly, Val, Leu, Arg, or Lys.

6. A polypeptide according to claim 1, wherein $X^1$ is a sequence of five amino acids with the structure EDCBA, wherein A is Glu or Asp; B is Glu, Asp, Val, Gly or Leu; C is Glu, Asp, Pro, Gly, Val, Leu, Arg, or Lys; D is Glu, Asp, Pro, Gly, Val, Leu, Arg, or Lys; and E is Glu, Asp, Pro, Gly, Val, Leu, Arg, or Lys.

7. A polypeptide according to claim 1, wherein $X^1$ is a sequence of six amino acids with the structure FEDCBA, wherein A is Glu or Asp; B is Glu, Asp, Val, Gly or Leu; C is Glu, Asp, Pro, Gly, Val, Leu, Arg, or Lys; D is Glu, Asp, Pro, Gly, Val, Leu, Arg, or Lys; E is Glu, Asp, Pro, Gly, Val, Leu, Arg, or Lys; and F is Glu, Asp, Pro, Gly, Val, Leu, Arg, or Lys.

8. A polypeptide according to claim 1, wherein $X^4$ is Glu or Asp.

9. A polypeptide according to claim 1, wherein $X^4$ is a sequence of two amino acids with the structure AB, wherein A is Glu or Asp, and B is Glu, Asp, Val, Gly or Leu.

10. A polypeptide according to claim 1, wherein $X^4$ is a sequence of three amino acids with the structure ABC, wherein A is Glu or Asp; B is Glu, Asp, Val, Gly or Leu; and C is Glu, Asp, Pro, Gly, Val, Leu, Arg, or Lys.

11. A polypeptide according to claim 1, wherein $X^4$ is a sequence of four amino acids with the structure ABCD, wherein A is Glu or Asp; B is Glu, ASP, Val, Gly or Leu; C is Glu, Asp, Pro, Gly, Val, Leu, Arg, or Lys; and D is Glu, Asp, Pro, Gly, Val, Leu, Arg, or Lys.

12. A polypeptide according to claim 1, wherein $X^4$ is a sequence of five amino acids with the structure ABCDE, wherein A is Glu or Asp; B is Glu, Asp, Val, Gly or Leu; C is Glu, Asp, Pro, Gly, Val, Leu, Arg, or Lys; D is Glu, Asp, Pro, Gly, Val, Leu, Arg, or Lys; and E is Glu, Asp, Pro, Gly, Val, Leu, Arg, or Lys.

13. A polypeptide according to claim 1, wherein $X^4$ is a sequence of six amino acids with the structure ABCDEF, wherein A is Glu or Asp; B is Glu, Asp, Val, Gly or Leu; C is Glu, Asp, Pro, Gly, Val, Leu, Arg or Lys D is Glu, Asp, Pro, Gly, Val, Leu, Arg, or Lys; E is Glu, Asp, Pro, Gly, Val, Leu, Arg, or Lys; and F is Glu, Asp, Pro, Gly, Val, Leu, Arg, or Lys.

14. A polypeptide according to claim 1, wherein, when $X^1$ or $X^4$ is more than 1 amino acid, the amino acid of $X^1$ immediately adjacent to $X^2$ is Glu or Asp, the amino acid of $X^4$ immediately adjacent to $X^3$ is Glu or Asp, or both are Glu or Asp.

15. A polypeptide according to claim 1, wherein, when $X^1$ or $X^4$ is more than 1 amino acid, either $X^1$ or $X^4$ comprise more than one Glu or Asp.

16. A polypeptide according to claim 1, wherein $X^1$ and $X^4$ both are at least 1 amino acid.

17. A polypeptide according to claim 16, wherein $X^1$ and $X^4$ are symmetrically identical, extending outwards from $X^2$ and $X^3$ respectively.

18. A polypeptide according to claim 1, wherein, when $X^4$ is one or more amino acids, an additional processing site is provided between $X^4$ and the N-terminal end of the heterologous protein.

19. A polypeptide according to claim 1, wherein the signal peptide is the α-factor signal peptide, the signal peptide of mouse salivary amylase, the carboxypeptidase signal peptide, or the yeast BAR1 signal peptide.

20. A polypeptide according to claim 1, wherein the leader peptide is a natural leader peptide.

21. A polypeptide according to claim 20, wherein the natural leader peptide is alpha-factor leader peptide.

22. A polypeptide according to claim 1, wherein the leader peptide is a synthetic leader peptide.

23. A polypeptide according to claim 22, wherein the synthetic leader peptide is selected from the group consisting of A: Ala-Pro-Val-Thr-Gly-Asp-Glu-Ser-Ser-Val-Glu-Ile-Pro-Glu-Glu-Ser-Leu-Ile-Gly-Phe-Leu-Asp-Leu-Ala-Gly-Glu-Glu-Ile-Ala-Glu-Asn-Thr-Thr-Leu-Ala;

B: Ala-Pro-Val-Thr-Gly-Asp-Glu-Ser-Ser-Val-Glu-Ile-Pro-Glu-Glu-Ser-Leu-Ile-Ile-Ala-Glu-Asn-Thr-Thr-Leu-Ala;

C: Ala-Pro-Val-Thr-Gly-Asp-Glu-Ser-Ser-Val-Glu-Ile-Pro-Ile-Ala-Glu-Asn-Thr-Thr-Leu-Ala;

D: Ala-Pro-Val-Thr-Gly-Asp-Glu-Ser-Ser-Val-Glu-Ile-Pro-Glu-Glu-Ser-Leu-Ile-Ile-Ala-Glu-Asn-Thr-Thr-Leu-Ala-Asn-Val-Ala-Met-Ala; and E: Gln-Pro-Val-Thr-Gly-Asp-Glu-Ser-Ser-Val-Glu-Ile-Pro-Glu-Glu-Ser-Leu-Ile-Ile-Ala-Glu-Asn-Thr-Thr-Leu-Ala-Asn-Val-Ala-Met-Ala.

24. A polypeptide according to claim 1, wherein the heterologous protein or polypeptide is selected from the group consisting of aprotinin or other protease inhibitors, insulin and insulin precursors, human or bovine growth hormone, interleukin, tissue plasminogen activator, glucagon, Factor VII, Factor VIII, Factor XIII, platelet-derived growth factor, enzymes, and a functional analogue of any of these proteins.

25. A polypeptide according to claim 24, wherein the heterologous protein or polypeptide is aprotinin or a functional analogue thereof.

26. A polypeptide according to claim 25, wherein $X^1$ is Glu-Arg-Leu-Glu or Lys-Glu-Leu-Glu.

27. A polypeptide according to claim 25, wherein $X^4$ is Glu-Leu or Glu-Leu-Asp-Leu.

28. A polypeptide according to claim 24, wherein the heterologous protein or polypeptide is insulin or an insulin precursor or a functional analogue thereof.

29. A polypeptide according to claim 28, wherein $X^1$ is Glu-Arg-Leu-Glu or Lys-Glu-Leu-Glu.

30. A polypeptide according to claim 28, wherein $X^4$ is Glu.

31. A polypeptide according to claim 28, wherein the heterologous protein or polypeptide is the insulin analogue precursor B(1-29)-AlaAlaLys-A(1-21), and wherein $X^1$ is Lys-Glu-Leu-Glu.

32. A polypeptide according to claim 28, wherein the heterologous protein or polypeptide is the insulin analogue precursor B(1-29)-SerAspAspAlaLys-A(1-21), and wherein $X^1$ is Lys-Glu-Leu-Glu.

33. A polypeptide comprising a fusion of a signal peptide, a leader peptide and heterologous protein or polypeptide, the polypeptide having the following structure:

signal peptide-leader peptide-$X^1X^2X^3X^4$-heterologous protein wherein $X^1$ is part of the leader peptide and is one or more amino acids which may be the same or different, $X^2$ and $X^3$ are the same or different and $X^2$ and $X^3$ are each a basic amino acid selected from the group consisting of Lys and Arg, $X^2$ and $X^3$ together defining a yeast processing site, and $X^4$ is part of the heterologous protein and is one or more amino acids which may be the same or different, which the proviso that at least one of the amino acids of $X^1$ and $X^4$ is a negatively charged amino acid selected from the group consisting of Glu and Asp, and that when the signal and leader peptide is the MFα prepro peptide and wherein $X^1$ is a peptide bond, $X^4$ is not Glu-Ala-Glu-Ala or Glu-Ala-Glu-Ala-Ser-Leu-Asp, and that when $X^4$ is a peptide bond, $X^1$ is not Ser-Leu-Asp.

34. A polypeptide comprising a fusion of a signal peptide, a leader peptide and a heterologous protein or polypeptide, the polypeptide having the following structure:

signal peptide-leader peptide-$X^1$ $X^2X^3X^4$-heterologous protein wherein $X^1$ is part of the leader peptide and is one or more amino acids which may be the same or different, $X^2$ and $X^3$ are the same or different and $X^2$ and $X^3$ are each a basic amino acid selected from the group consisting of Lys and Arg, $X^2$ and $X^3$ together defining a yeast processing site, and $X^4$ is part of the heterologous protein and is one or more amino acids which may be the same or different, with the proviso that at least one of the amino acids of $X^1$ or $X^4$ is a negatively charged amino acid selected from the group consisting of Glu and Asp, and that when the signal and leader peptide is the MFα prepro peptide add wherein $X^1$ is a peptide bond, $X^4$ is not Glu-Ala-Glu-Ala or Glu-Ala-Glu-Ala-Ser-Leu-Asp, and that when $X^4$ is a peptide bond, $X^1$ is not Ser-Leu-Asp.

35. A polypeptide according to claim 1, wherein, when $X^1$ and $X^4$ are each more than 1 amino acid, the amino acid of $X^1$ immediately adjacent to $X^2$ is Glu or Asp, the amino acid of $X^4$ immediately adjacent to $X^3$ is Glu or Asp, or both are Glu or Asp.

36. A polypeptide according to claim 1, wherein, when $X^1$ and $X^4$ are each more than 1 amino acid, $X^1$ or $X^4$ comprise more than one Glu or Asp.

37. A polypeptide according to claim 1, wherein, when $X^1$ and $X^4$ are each more than 1 amino acid, $X^1$ and $X^4$ comprise more than one Glu or Asp.

38. An aprotinin analogue of the general formula $X^4$-aprotinin(1-58), wherein $X^4$ is an N-terminal extension by one or more amino acids at least one of which is a negatively charged amino acid selected from the group consisting of Glu and Asp.

39. An analogue according to claim 38, wherein $X^4$ is Glu or Asp.

40. An analogue according to claim 38, wherein $X^4$ is a sequence of two amino acids with the structure AB, wherein A is Glu or Asp, and B is Glu, Asp, Val, Gly or Leu.

41. An analogue according to claim 38, wherein $X^4$ is a sequence of three amino acids with the structure ABC, wherein A is Glu or Asp; and B is Glu, Asp, Val, Gly or Leu; and C is Glu, Asp, Pro, Gly, Val, Leu, Arg, or Lys.

42. An analogue according to claim 38, wherein $X^4$ is a sequence of four amino acids with the structure ABCD, wherein A is Glu or Asp; B is Glu, Asp, Val, Gly or Leu; C is Glu, Asp, Pro, Gly, Val, Leu, Arg, or Lys; and D is Glu, Asp, Pro, Gly, Val, Leu, Arg, or Lys.

43. An analogue according to claim 38, wherein $X^4$ is a sequence of five amino acids with the structure ABCDE, wherein A is Glu or Asp; B is Glu, Asp, Val, Gly or Leu; C is Glu, Asp, Pro, Gly, Val, Leu, Arg, or Lys; D is Glu, Asp, Pro, Gly, Val, Leu, Arg, or Lys; and E is Glu, Asp, Pro, Gly, Val, Leu, Arg, or Lys.

44. An analogue according to claim 38, wherein $X^4$ is a sequence of six amino acids with the structure ABCDEF, wherein A is Glu or Asp; B is Glu, Asp, Val, Gly or Leu; C is Glu, Asp, Pro, Gly, Val, Leu, Arg, or Lys; D is Glu, Asp, Pro, Gly, Val, Leu, Arg, or Lys; E is Glu, Asp, Pro, Gly, Val, Leu, Arg, or Lys, and F is Glu, Asp, Pro, Gly, Val, Leu, Arg, or Lys.

45. A analogue according to claim 38, wherein, when $X^4$ is more than 1 amino acid, $X^4$ comprises more than one Glu or Asp.

46. An analogue according to claim 38, wherein $X^4$ is Glu-Leu or Glu-Leu-Asp-Leu.

* * * * *